United States Patent
Gates et al.

(10) Patent No.: US 11,031,135 B2
(45) Date of Patent: Jun. 8, 2021

(54) DETERMINATION OF CYBERSECURITY RECOMMENDATIONS

(71) Applicant: Edge2020 LLC, Herndon, VA (US)

(72) Inventors: Tell Gates, Great Falls, VA (US); Ronald Hirsch, Herndon, VA (US)

(73) Assignee: Edge2020 LLC, Herndon, VA (US)

( * ) Notice: Subject to any disclaimer, the term of this patent is extended or adjusted under 35 U.S.C. 154(b) by 280 days.

(21) Appl. No.: 16/143,093

(22) Filed: Sep. 26, 2018

(65) Prior Publication Data
US 2019/0098039 A1    Mar. 28, 2019

Related U.S. Application Data

(60) Provisional application No. 62/563,448, filed on Sep. 26, 2017.

(51) Int. Cl.
| | |
|---|---|
| H04L 29/06 | (2006.01) |
| G16H 50/20 | (2018.01) |
| G06N 3/08 | (2006.01) |
| G06N 3/04 | (2006.01) |
| G16H 20/70 | (2018.01) |
| G16H 20/40 | (2018.01) |
| G16H 20/10 | (2018.01) |

(Continued)

(52) U.S. Cl.
CPC ......... *G16H 50/20* (2018.01); *G06F 21/6245* (2013.01); *G06N 3/0427* (2013.01); *G06N 3/08* (2013.01); *G06N 3/088* (2013.01); *G16H 20/10* (2018.01); *G16H 20/40* (2018.01); *G16H 20/70* (2018.01); *G16H 50/70* (2018.01); *G16H 70/00* (2018.01); *H04L 63/0407* (2013.01); *H04L 63/1433* (2013.01); *H04L 63/1441* (2013.01); *H04L 63/0428* (2013.01)

(58) Field of Classification Search
CPC .... G06F 21/6245; G06F 21/577; G06F 21/60; G06N 3/08; G06N 3/088; H04L 63/1433; H04L 63/1441; H04L 63/1416
See application file for complete search history.

(56) References Cited

U.S. PATENT DOCUMENTS

| | | | |
|---|---|---|---|
| 8,726,393 B2* | 5/2014 | Macy ................. | G06Q 10/0635 726/25 |
| 8,793,790 B2* | 7/2014 | Khurana ............ | G07C 9/00571 726/22 |

(Continued)

*Primary Examiner* — Hosuk Song
(74) *Attorney, Agent, or Firm* — The Watson IP Group, PLC; Dan Fiul

(57) ABSTRACT

A method and apparatus can include a system controller and a system processor. The system controller can retrieve a cybersecurity dataset from at least one database, the retrieved dataset including information associated with at least one element associated with at least one of network traffic and process monitoring of at least one process being implemented in at least one network element. The system processor can utilize multidimensional nonlinear manifold clustering on the at least one element of the retrieved cybersecurity dataset, assign a threat entity formulated from the at least one element of the retrieved dataset into a cybersecurity threat hyper-volume based on the multidimensional nonlinear manifold clustering, and formulate a recommended action to be taken based on the assignment of the threat entity into the cybersecurity threat hyper-volume.

42 Claims, 4 Drawing Sheets

(51) Int. Cl.
*G06F 21/62* (2013.01)
*G16H 50/70* (2018.01)
*G16H 70/00* (2018.01)

(56) References Cited

U.S. PATENT DOCUMENTS

| | | | | |
|---|---|---|---|---|
| 8,793,799 | B2* | 7/2014 | Fritzson | H04L 63/1441 |
| | | | | 726/25 |
| 8,800,037 | B2* | 8/2014 | Paek | H04L 63/1416 |
| | | | | 726/23 |
| 8,850,565 | B2* | 9/2014 | Patrick | H04L 63/1441 |
| | | | | 726/22 |
| 8,914,880 | B2* | 12/2014 | Lee | G06F 21/577 |
| | | | | 726/22 |
| 9,032,521 | B2* | 5/2015 | Amini | H04L 63/1433 |
| | | | | 726/23 |
| 9,537,884 | B1* | 1/2017 | Raugas | H04L 63/1433 |
| 10,721,254 | B2* | 7/2020 | Kotinas | G06K 9/6218 |

* cited by examiner

DETERMINATION OF CYBERSECURITY RECOMMENDATIONS

This application claims priority to U.S. Provisional Application No. 62/563,448, entitled "CLUSTERING AND ADJUDICATION TO DETERMINE DECISIONS FOR MULTIPLE APPLICATIONS", filed on Sep. 26, 2017, to Hirsch et al., the entirety of which is expressly incorporated herein by reference.

BACKGROUND

1. Field

Applicant's disclosed features provide such a real-world technical benefit to a real-world technical deficiency within the art of cybersecurity. More particularly, the present disclosure is directed to an apparatus and method for determining tiered responses to such threats.

2. Introduction

The challenges in cybersecurity are constantly evolving with new threats. These challenges can include attacks from external hackers, insider threats, misconfigured security settings, etc. These challenges require new methods that can (1) more rapidly diagnose and/or identify new threats, (2) identify potential threatening user behavior, and/or (3) reduce the number of data loss occurrences and amount of data while minimizing the number of false alarms that plague current cybersecurity systems.

BRIEF DESCRIPTION OF THE DRAWINGS

In order to describe the manner in which advantages and features of the disclosure can be obtained, a description of the disclosure is rendered by reference to specific embodiments thereof which are illustrated in the appended drawings. These drawings depict only example embodiments of the disclosure and are not therefore to be considered to be limiting of its scope.

DETAILED DESCRIPTION

The key to understanding the challenges and developing an effective cybersecurity solution can be contained in not only analyzing network traffic, but also analyzing user interaction, external user influences, on-going cybersecurity research, user and other relevant social media, etc. The method and apparatus presented in the embodiments disclosed herein can make use of a novel approach to machine learning (and/or deep learning) to protect network resources and critical data on those network resources.

A disclosed herein CyberSecurity Support System (CSSS) 100 can perform advanced analytics, including improvements to existing techniques and algorithms including, but not limited to, NonLinear Manifold (NLM) clustering, Statistical Decision Theory, Neural Networks and/or a combination of these to control processing by the CSSS 100 and data flow, and optimize the results obtained by such processing. The approach presented herein can optimize detection, characterization, and exploitation of obscure structures, patterns, information in the network traffic and network operations, and/or metadata associated with network traffic and network operations. Furthermore, this approach can discover confluence among cybersecurity relationships, processes, and/or events, which can be useful in making cybersecurity decisions, and recommendations, and taking an appropriate action in response thereto.

The computer-based methods, systems and apparatuses disclosed herein can provide for a decision to recommend action to be taken in response to a potential cybersecurity threat. There are many cybersecurity threats that can include phishing attacks, man-in-the-middle attacks, malware attack, coordinated and uncoordinated attacks, VLAN hopping, buffer overflow, SQL injection, etc. Recommended actions that can be taken in response to a cybersecurity threat include at least one of blocking access, block or disable a computer process, program, and/or application, lockout a user, slowdown and/or delay access, isolate the threat, alert a network administrator, alert a user, not take any action at all, etc. The computer-based methods, systems and apparatuses disclosed herein can also provide for selection of cost-effective and resource-efficient decisions for cybersecurity. Decision, discovery, detection, and identification, are used interchangeably herein. The CSSS 100, discussed in detail below, can be used for corporate networks, as an external service for home and business (provided by Internet Service Providers, etc.), utility and similar infrastructure (refineries, manufacturing, etc.), etc. to detect and protect against cybersecurity threats.

Figure 1:
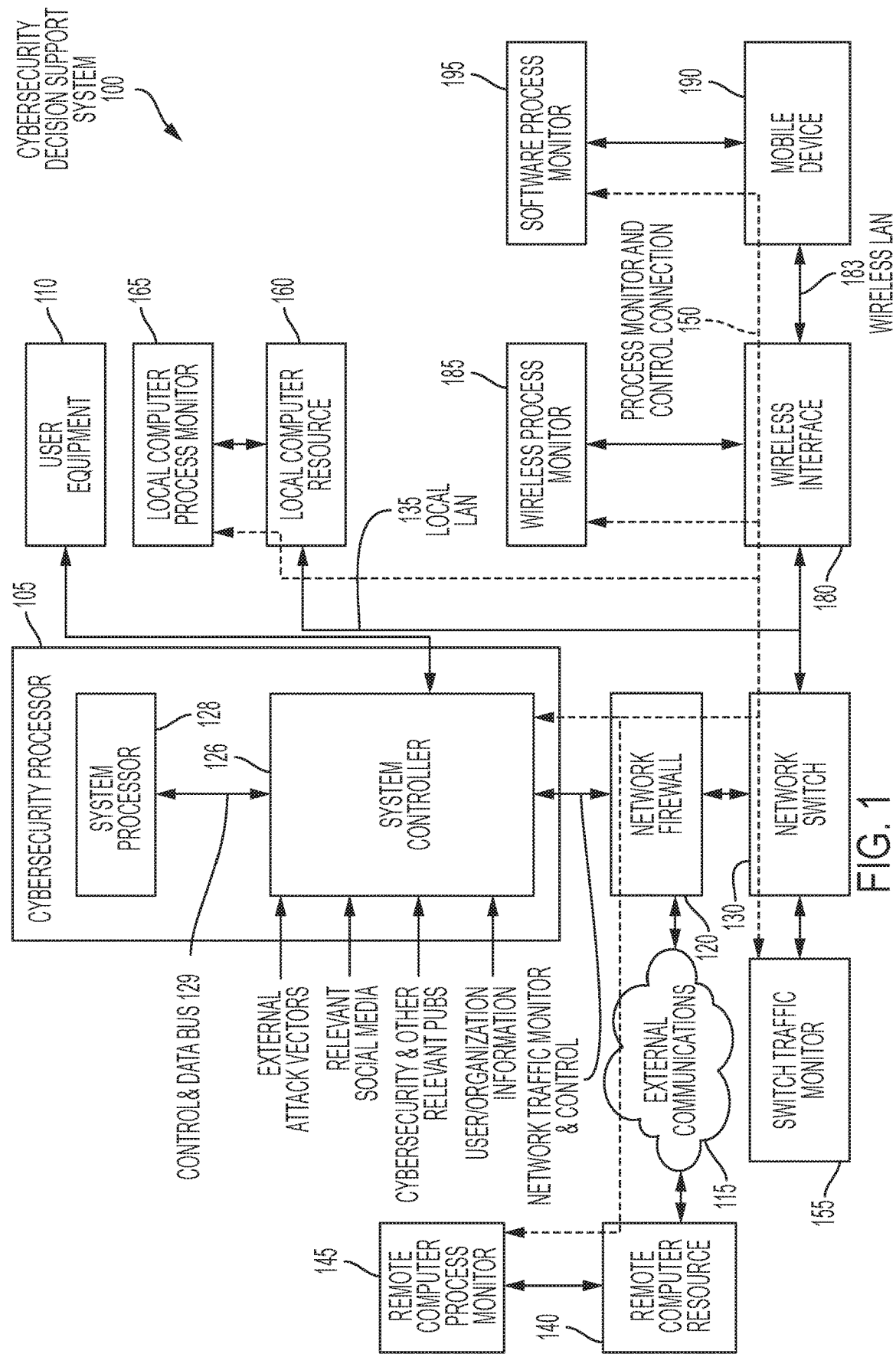
FIG. 1 illustrates an example of an CyberSecurity Support System, in accordance with one or more possible embodiments.

FIG. 1 illustrates an example of the CSSS 100, in accordance with one or more possible embodiments. In particular, a CyberSecurity Processor (CSP) 105 can monitor all communications through a network firewall 120 residing between a local computer resource 160 (servers, computers, Virtual Machines (VM), cloud-based infrastructure, Internet of Things (IoT), Point of Sale (POS) devices, a mobile device 190 (laptop, smart phone, tablets, wearables, etc.), and a remote computer resource 140 (including remote mobile devices (not shown)) that can be accessed via an external communications 115 which can include the Internet, a Virtual Private Network (VPN), Wide Area Network (WAN), wireless communications, point-to-point communications, and/or any other dedicated communication resources. The network firewall 120 can be connected via a network switch 130 to the local computer resource 160 and/or a wireless interface 180 for access by the mobile device 190.

For example and as discussed in further detail herein, the system controller 126 can retrieve a cybersecurity dataset from at least one database, the retrieved dataset (hereafter referenced as retrieved dataset) including at least one element associated with at least one of network traffic and process monitoring of at least one process being implemented in at least one network element. The at least one element of the retrieved dataset can further includes user background information, network policy, and cybersecurity publications. In at least one embodiment, the system controller 126 can further transmit to a user equipment (UE) 110, such as a personal computer (PC), a tablet computer, a smart phone, augmented reality interface, or any other digital device that can receive and display digital information, a recommendation (recommended action) to be taken in response to a cybersecurity threat, including the cybersecurity outputs given in Table 6. The UE 110 can also provide control and feedback from input devices, such as a keyboard, mouse, eye and hand movement sensors, etc. In at least one embodiment, the system controller 126 can further transmit a recommendation command that implements the recommendation, such a recommendation command can be transmitted to the network element, such as the network firewall 120, the network switch 130, a switch traffic monitor 155, the local computer resource 160, a local computer process monitor 165, the wireless interface 180, a wireless process monitor 185, mobile device 190, software process monitor 195, remote computer resource 140, and/or remote computer process monitor 145. This recommendation command can be transmitted via a local LAN 135, a process monitor and control connection 150, such as a bus, external communications 115, or any other available communications interface. In at least one embodiment, the recommendation command, formulated in response to formulating the recommended action, can include at least one of block IP address, block access, block process, block a port, isolate, lockout user, slowdown/delay access, alert the network administrator, alert the user, and do not take an action. The recommended actions can be implemented with a settable time limit.

Figure 2:
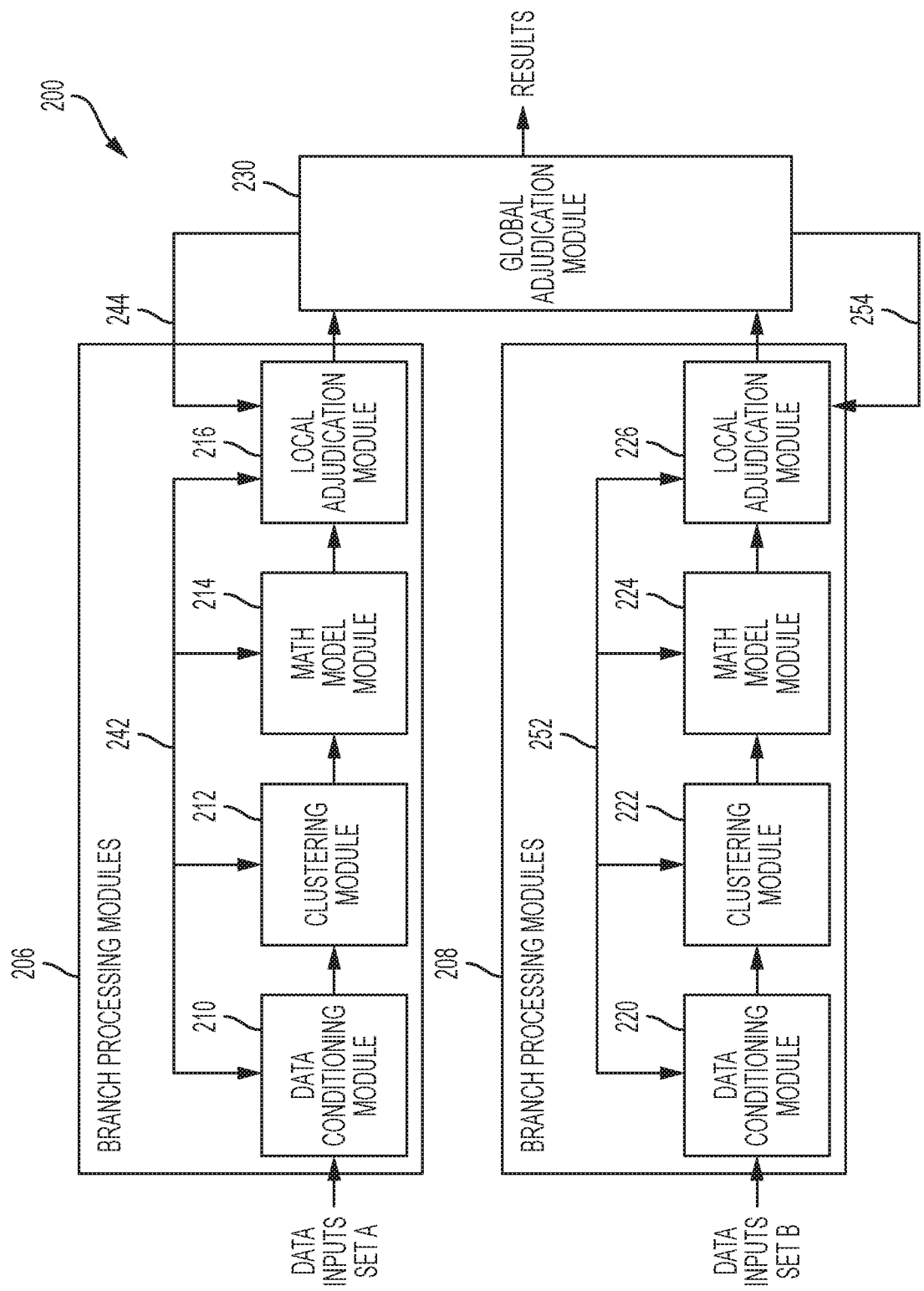
FIG. 2 illustrates an example advanced analytics method, in accordance with one or more possible embodiments.

For example and as discussed further herein, the system processor 128 can generate an entity (feature vector) from the data in the Tables 1-6. In the detailed analysis mode, clustering is used to insert entities into an multidimensional entity universe. The clustering process, along with adjudication, and training can be used to define a cybersecurity hyper-volume contained in the entity universe. The types of cybersecurity hyper-volumes can include threat, non-threat, and other types (potential threat, unknown threat, etc.). In the real-time mode, the system processor 128 can insert the entities as they are generated into the entity universe by direct insertion and/or Monte Carlo insertion. The entity can be then identified as a threat, non-threat, and other types (potential threat, unknown threat, etc.) of entity based on the type of cybersecurity hyper-volume from the detailed analysis mode, in which the entity is inserted. If the entity is inserted, outside any previously identified cybersecurity hypervolume, it is considered an indeterminant entity. Threat entity can include threat entity, potential threat entity, unknown threat entity, etc. and can generate a recommended action. An indeterminant entity can be a threat or non-threat entity depending on its direct insertion or final Monte Carlo position, nearness to other threat and nontreat hyper-volumes, network policy, etc. In an example, the system processor 128 can formulate a cybersecurity threat entity (hereafter referenced as the threat entity), cybersecurity non-threat entity (hereafter referenced as the non-threat entity), etc. from the retrieved dataset. The retrieved dataset can include a previously formed threat entity and/or non-threat entity, as well as raw data that can be used to form the threat entity and/or non-threat entity in the data conditioning modules 210 and 220 (FIG. 2).

The CSP 105 can include a system controller 126 and a system processor 128 coupled to each other via a bi-directional control, status and data bus 129. For example and as discussed in further detail herein, the system processor 128 can perform various processes as a basis for determining the recommendation of at least one of response to at least one cybersecurity threat, both simultaneous and consecutive. Thereafter, the system processor 128 can generate the recommendation command, in response to the recommendation, to implement the recommendation. The system processor 128 can utilize multidimensional nonlinear manifold clustering on at least one element of the retrieved dataset, can assign a threat entity, which can be formulated from the at least one element of the retrieved dataset, into a cybersecurity threat hyper-volume based on the multidimensional nonlinear manifold clustering, and can formulate the recommended action to be taken based on the assignment of the threat entity into the cybersecurity threat hyper-volume.

In an example, the system processor 128 can divide the entity into two or more sub-entities. As an example, an entity could have conflicting information that could inadvertently insert it into a cybersecurity threat hyper-volume. However, splitting this entity into sub-entities to separate the conflicting information and thereafter reinserting the sub-entities into the entity universe could subsequently show that the original entity was not a threat.

For example and as discussed further herein, the system processor 128 can perform adjudication to minimize a loss function in order to optimize the assignment of the threat entity and/or non-threat entity by adjusting a decision boundary of the cybersecurity threat hyper-volume for the multidimensional nonlinear manifold clustering and at least one other type of multidimensional clustering including at least one of linear clustering, linear manifold clustering, and nonlinear clustering. The adjudication boundary adjustment of the cybersecurity threat hyper-volume can improve the separation of threats and non-threats in the entity universe. The adjudication can be done locally and/or across the entity universe. The adjudication can improve the detection of cybersecurity threats while minimizing the probability of a false alarm. The risk tolerance network policy established by the network administrator can also be used to influence the adjudication boundary adjustment that can change the assignment of the threat entity. As an example, the adjudication with a risk tolerance network policy that is more conservative, (i.e. more concerned with a network attack than a false alarm) can enlarge the cybersecurity threat hyper-volume.

For example and as discussed further herein, the system processor 128 can utilize the multidimensional nonlinear manifold clustering and/or at least one other type of multi-dimensional clustering, based on a minimizing the loss function to optimize assignment of any of the threat, non-threat, and other type (potential threat, unknown threat, etc.) of entity. In an example, the assignment of the threat entity into the cybersecurity threat hyper-volume can be further based on at least one other type of multidimensional clustering including at least one of linear clustering, linear manifold clustering, and nonlinear clustering. The system processor 128 can utilize a neural network to define the cybersecurity threat hyper-volume, and any of the other type of hyper-volumes described herein. In another example, the system processor 128 can perform adjudication to control a number of iterations of the selection of the retrieved dataset and/or entity. In an example, the system processor 128 can compare multiple iterations of the multidimensional nonlinear manifold clustering and at least one other type of multidimensional clustering, such as at least one of linear clustering, linear manifold clustering, and nonlinear clustering. The system processor 128 can formulate a confidence region to rank order a plurality of the recommendation of at least one of cybersecurity response. The system processor 128 can ascribe a recommended action to the cybersecurity threat hyper-volume based on at least one of supervised training and unsupervised training. The system processor 128 can perform adjudication to generate the entity to optimize the recommendation of at least one of block IP address, block access, block processes, block port, isolate, lockout user, slow down/delay access, slowdown/delay process, and alert the network administrator, alert the user, and do not take an action, generate the recommended actions.

For example and as discussed further herein, the system processor 128 can performs adjudication to minimize a loss function in order to optimize the assignment of the threat entity by adjusting a decision boundary of the cybersecurity threat hyper-volume for the multidimensional nonlinear manifold clustering and at least one other type of multidimensional clustering including at least one of linear clustering, linear manifold clustering, and nonlinear clustering, and selects at least one of the multidimensional nonlinear manifold clustering and the at least one other type of multidimensional clustering based on a minimum loss function and optimum threat entity assignment. The system processor 128 can performs adjudication to control a number of iterations of the selection of the retrieved dataset and compare multiple iterations of the multidimensional nonlinear manifold clustering and at least one other type of multidimensional clustering. The system processor 218 can place the threat entity into an entity universe based on direct insertion. The system processor 128 can place the threat entity into an entity universe based on Monte Carlo insertion with or without measure of importance. The system processor 128 can divide the threat entity into two or more sub-entities. The system processor 128 can combine multiple entities into a super-entity. The system processor 128 can generate the threat entity using text processing including performing at least one of Information Theoretic, semantic, and syntactic, with the entity generation includes extracting numerically encoded text features from at least one of bulk text, structured text, and unstructured text. The system processor 128 can perform adjudication to formulate at least one of the retrieved dataset and the threat entity, to optimize the recommended action. In an example, a network element can be at least one of a network firewall, a network switch, a mobile device, a local computer resource, a remote computer resource, a user equipment, and a wireless interface.

In at least one embodiment, the CSP 105 can use the NLM clustering and adjudication to define non-threat hyper-volumes. Entities that fall outside the non-threat hyper-volumes can be considered cybersecurity threats and acted on appropriately.

Throughout this document, entities can be identified as a threat entity, a non-threat entity, or an indeterminate entity. An indeterminate entity can be an entity whose particular combination of attributes has not been specifically characterized as a threat or non-threat entity. An indeterminate entity can be treated as a cybersecurity threat based on similarity to other threats and indeterminant entity network policy.

Suspicious cybersecurity threats can be isolated. As an example, of this would be shunting the suspicious cybersecurity threats to the firewall demilitarized zone (DMZ) network and provide a computer resource that can emulate valid computer resources to further analyze the attack to improve future cybersecurity threat detection and the ascribed recommended action.

In particular, the system processor 128 can accept data from the system controller 126, organize selected working data and transfers the output to one or more table(s) and the decision/action/reasoning results to the system controller 126. The system processor 128 can accept as input data from one or more databases, the one or more databases made up of a variety of elements such as shown in Tables 1 through 4. All input data can be received from the system controller 126. The system processor 128 can output results to the system controller 126. The system processor 128 can be coupled to the system controller 126 and a system processor control and status 330 (FIG. 3), and system processor control, status, and data bus 332 which allows the system processor 128 to communicate with system processor storage 340 and the system controller 126 via the bi-directional control, status and data bus 129. The system processor 128 can use advanced analytics, predictive analysis, statistical inference and decision making as a basis for making cybersecurity decisions. Advanced analytics is the grouping and synergistic use of techniques to improve domain understanding, to predict future outcomes and using statistical inference for decision making. The system controller 126 can be in communication with the UE 110.

The local computer resource 160, including personal computers, servers, virtual machine instances, wired and wireless devices, including Internet of Things (JOT) devices, game consoles, smart phones, tablets, etc., are connected to a network than can comprise a Local Area Network (LAN) 135. Each local computer resources 160 can have a local computer process monitor 165 (where appropriate) coupled thereto to analyze the on-going processes and user interaction and report this activity to the CSP 105, via the process monitor and control connection 150. The local computer process monitor 165 can be implemented in hardware and/or software. In situations where the local computer process monitor 165 is not appropriate, such a monitoring function can be performed in the network firewall 120, a network switch 130, and switch traffic monitor 155. The hardware implementations of the local, wireless, software, and remote computer process monitor 165, 185, 195, and 145 can be performed in a module inside the local computer resource 160, remote computer resource 140, mobile device 190, and a remote mobile device, via a USB module or other external module that can be connected via a communications interface. The process monitor and control connection 150 can either be a dedicated connection, such as a parallel LAN, and/or can be a virtual process monitor connection using the local LAN 135.

Mobile device 190, in particular, but not limited to, laptops, smart phones, tablets, fitness devices, wireless Internet of Things (JOT) devices, etc., because of limits on battery usage and heat dissipation, generally can have limited processing capability. When interfacing devices with the network, a wireless process monitor 185 can monitor the data traffic to and from the mobile device for threats. In addition, a software process monitor 195 can be placed on the mobile to device to report activity to the wireless process monitor 185 to analyze the on-going processes and user interaction and report this activity to the CSP 105 via the process monitor and control connection 150. In mobile device 190 with sufficient processing resource, a software processor monitor 195 can be utilized on the mobile device 190, vs. in an external wireless processor monitor 185. In situations where the mobile device is using encrypted communications (e.g. hypertext transfer protocol secure (HTTPS), VPN, and other secure transmission communications, etc.), the wireless interface can decrypt and re-encrypt both of the incoming and outgoing communications to analyze the traffic in the wireless processor monitor 195 and have the mobile device 190 operate without a special mode. In at least one embodiment, the traffic encryption/decryption can be moved to a wireless interface 180 (e.g., a wireless router) coupled to a network switch 130 and the mobile device 190, so all data traffic can be analyzed in the wireless processor monitor 185. The process of decrypting a file, attachment, etc., verifying that there is no threat, and re-encrypting the file, attachment, etc. can be done in the network firewall 120, switch traffic monitor 155, wireless process monitor 185, and remote computer and local computer process monitors 145 and 165 to monitor all encrypted files that are received by the CSSS 100 from any source (firewall, memory stick, etc.).

The remote computer resource 140, including personal computers, servers, virtual machine instances, wired Internet of Things (IOT) devices, etc., and mobile device 190 are connected to the network firewall 120 via the external communications 115. Remote computer resource 140 can be computer resources connected individually, as part of a LAN, etc. to the network firewall 120. Remote computer resource 140 can have an optional remote computer process monitor 145 to analyze on-going processes and user interaction, and report this activity to the CSP 105 via the process monitor and control connection 150. Remote wireless devices (not shown) can operate with a remote wireless process monitor or a remote software process monitor, similar to the local LAN 135 side operation.

The system controller 126 can provide and/or retrieve selected data both from the processor monitor and control connection 150 and other information relating to relevant external publications, including cybersecurity journals, websites, government publications, etc., individual and/or corporate use/use history and risk factors, data sensitivity, social media and metadata and/or information, as well the results from Table 5, Prior Run Archive. The system controller 126 can provide the input application sensor metadata, databases, real-time data, interfaces to the system processor 128. The network administrator and/or other users (including domain expert) can control the CSP 105 through the system controller 126 via the UE 110. The system controller 126 can transfer cybersecurity threat decisions, recommended actions, adjudication, and reasoning from the system processor 128 to a user interface executing on the UE 110. The CSP 105 can operate under the control of the multi-level, hierarchical adjudication, shown in more detail in FIG. 2. In an enterprise configuration, CSPs 105 can be located in each of a plurality of the LAN 140. In at least one embodiment, such CSPs can operate interactively in conjunction with one another.

The system processor 128 can output results to the system controller 126. The system processor 128 can be coupled to the system controller 126 and a system processor control and status 330 (FIG. 3), and system processor control, status, and data bus 332 which allows the system processor 128 to communicate with system processor storage 340 and the system controller 126 via the bi-directional control and data 129. The system processor 128 can use advanced analytics, predictive analysis, statistical inference, change detection, detection and decision making described in FIG. 2 as a basis for making cybersecurity decisions to recommend or not recommend a cybersecurity threat. Advanced analytics is the grouping and synergistic use of techniques to improve domain understanding, to predict threats and network responses, using statistical inference and tracking. Indeterminate entities can be used to predict threats and network responses. The decision outputs can have multiple thresholds that can, for example, stop all traffic or kill a process, slow down traffic to limit a data spill, buffer traffic temporarily to allow more time for the CSP 105 to perform a more thorough analysis, alert the computer system administrator, highlight the activity for future investigation, continue to monitor potential threats, correlate suspicious activity in other parts of network, and/or do nothing. These threshold options can be done in the network firewall 120, local computer resource 160, the wireless interface 180, and/or in mobile device 190. The concept of slowing down traffic can also be accomplished by increasing the priority on traffic that has not been identified as a threat.

The system processor 128 can offer other process benefits which can provide real-world technical benefits to a real-world technical deficiency within the art. For example, automating time-consuming aspects of processing that can include: 1) finding interactions among disparate data sources that can be difficult to detect, 2) providing objective and repeatable decisions that can always "treat the same evidence in the same way", and/or 3) the data in Table 5—Prior Run Archive (shown below) can be made available anywhere in the processing.

Example Tables 1 through 6 can represent examples of input and output data and metadata that include the relationships, structures, patterns, time, location (physical, IP, etc.), other information, and reasoning for the CSP 105 defined herein. For example, Table 1 can provide the ongoing network traffic from the network firewall 120, the local computer process monitor 165, the wireless process monitor 185, and a software process monitor 195. The process monitoring 145, 165, and 195 can be for both local and/or remote computer resources 160 and 140, respectively and local and/or remote mobile device 190 and (remote mobile devices not shown).

Table 2 can include process monitor inputs from local and remote computer resources, mobile device 190, IOT, etc. Table 3 can include user information. A user can be defined as at least one of an individual, a corporation, a laboratory, a university, etc. Table 4 can include information from cybersecurity and other relevant publications, and Table 5 can include prior run archive information. One of ordinary skill within the art understands that such information from Tables 1 through 4 are examples of cybersecurity related information, and that Tables 1 through 4 can include any other cybersecurity information that can be used to make a recommendation to take action (recommended action) based on a cybersecurity threat. Thus, the computer-based methods, systems and apparatuses disclosed herein can provide decisions as applied to cybersecurity applications and recommend an appropriate action based on such decisions. The input and output data for cybersecurity applications can be interrelated. Tables 1 through 6 can be linked both forward (e.g. individual CSSS 100 instances to a central CSSS 100 instance to consolidate information from many sites) and in reverse (e.g. central CSSS 100 to individual CSSS 100 instances). In at least one embodiment, threat entities that represent attack, suspicious activity, etc. and non-threats can be shared between multiple instances of the CSP 105.

Note all information in these entities, such as individual users, attack vectors, etc., that are defined by feature vectors (entities) can share at least one common attribute. The cybersecurity hyper-volume is the defined multidimensional space that is enclosed by a multidimensional surface (boundary) that identifies entities that share like and/or similar attributes. The more attributes that a particular entity shares (that is, have in common) with other entities in a particular cybersecurity threat hyper-volume, the higher the confidence of the decision and entity assignment to the particular cybersecurity threat hyper-volume.

Figure 3:
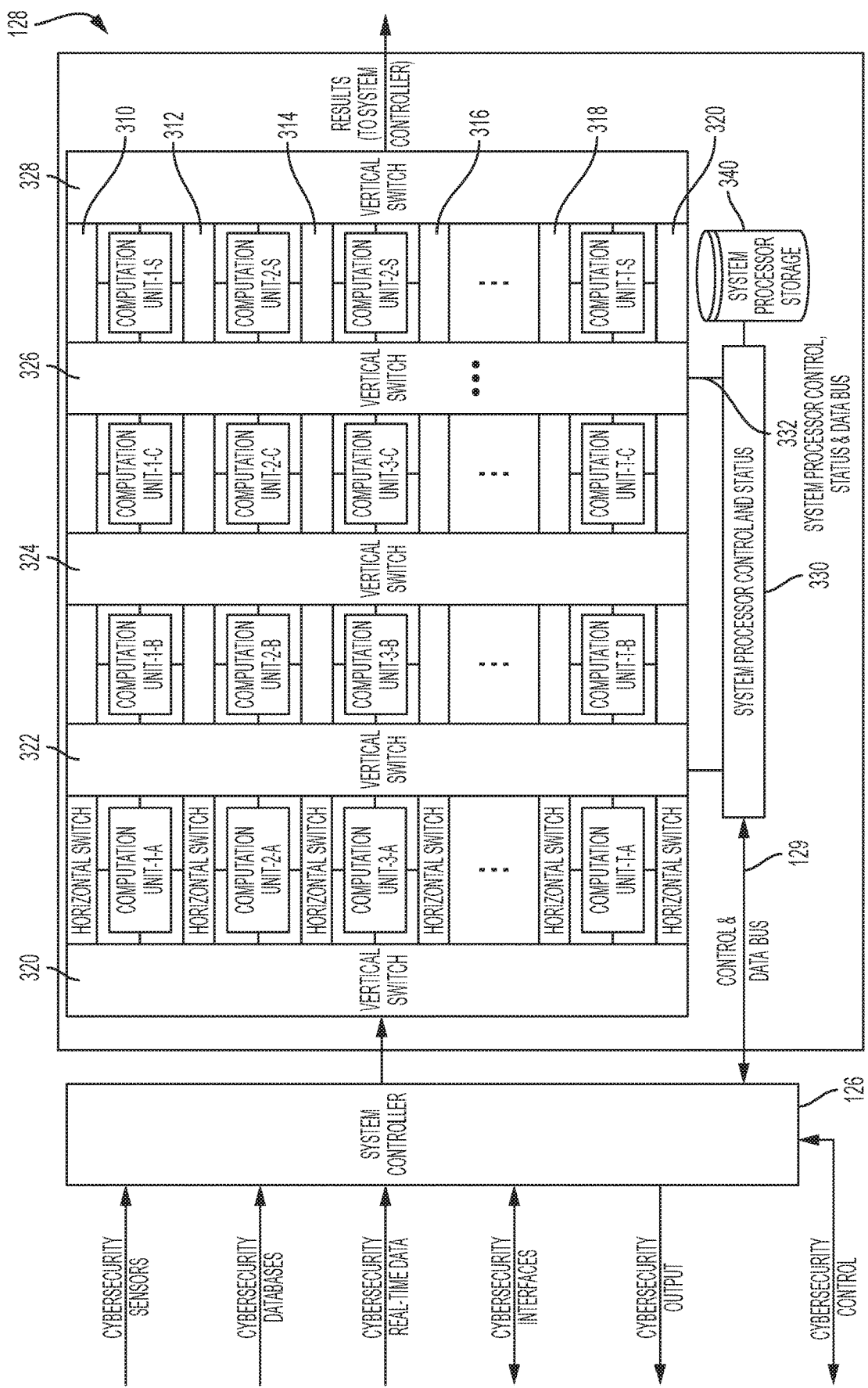
FIG. 3 illustrates an example system processor implementation, in accordance with one or more possible embodiments.

All input and/or output tables, such as Tables 1 through 6, can include data/metadata and/or graphical data (including maps, graphs, charts, etc.). Table 5—Prior Run Archive can contain an archive of all input, metadata, graphical data, intermediate results, and output information associated with each processing run. This information can be stored in the system processor storage 340 (FIG. 3).

Using a multistage, iterative adjudication processing, any information in the output tables can be combined with any selected data/metadata in the input and prior run archive tables for multiple cybersecurity decisions and appropriate recommended action. For example, an identified network attack vector and/or portion of a network attack vector can be utilized in a subsequent analysis run. Data can be processed, in serial, in parallel and/or in combination of these. Data/metadata in any of the Tables 1 through 6 can be encrypted and/or randomized, as necessary, to ensure privacy.

All data within Tables 1 through 5 can be updated over time and as cybersecurity threat detection techniques, attacks, etc. evolve. Such data can be tracked over short intervals, as well as an months and years (the tracking can be forward and backward). Also, data can be multi-scale, for example short high-speed attacks or long slow attacks, etc., or a combination of these.

TABLE 1

Network Inputs

Network ID
Network Topology (History, Current, Planned,)
Packet Data
Packet Type (TCP, UDP, IP, etc.)
Port
Other Header Information (Source address, destination address, header size, packet size, port, etc.)
Payload Signature
Certificates
OSI Layer
Network load
Network Topology
Firewall, Switch, Printer, etc. (Manufacturer, Model Number, Serial Number, Date of Manufacture, Location, etc.
Processor/Operating System/Software (version)/Other Hardware, etc.
Local and Remote Computer Resources and Mobile Devices (Manufacturer, Model Number, Serial Number, Date of Manufacture, Location, etc.
Processor Manufacturer and model number
Operating System including patch level
Programs (Available and Loaded), version number, release date
Other processor hardware (Motherboard devices/accessed externally)
Equipment Vulnerabilities
Packet History (Tracking similar traffic by source ID, destination ID, traffic type, route, latency, jitter, port, time between packets, etc.)
Tagged Packets
Shadow Networks
Malware Signatures
Virus Signatures
Network Intrusion Defenses (History, Current,)
Network Attacks/Cybersecurity Threat Entities (History)
Network Breach Cost (History, Current,)
Network Breach Insurance Cost (History, Current)
Network Breach Liability Cost (History, Current, Projected)
Other Network Defenses Hardware & Expenditures (History, Current)
Other Network Defenses Software & Expenditures (History, Current)
Identification and Location of Sensitive Data & Value (History, Current)
Event Audit Trail (History, Current)
Network Policies (risk, indeterminant threat handling, etc.)
Physical Monitoring (Access control, facial recognition, voice recognition, etc.)

TABLE 2

Process Monitor Inputs

Network ID monitor
User ID monitor

TABLE 2-continued

Process Monitor Inputs

Computer Resource ID monitor
File Access monitor
Session ID monitor
Stack Threads (start up and exit, status codes, etc.) monitor
Input/Output (disk, ports, keyboard, USB, etc.) monitor
Process/software/app program image load monitor

TABLE 3

User Information

User ID (History, Current, Planned) - Department/Trusted External Organization (company, corporation, university, etc.), Employee/Subcontractor/, Function, Purpose, Trust Level, Location (Geographic and IP Address), Use Time Tag, Use Interval, Audit Trail, characteristics of user keyboard use, mouse use, window organization, documents routinely accessed
Name (s) and Aliases, Reason & When
Employee Evaluations/Assessment (History, Current)
Employee Position & Changes (History, Current)
Schedule of network interaction - i.e., employing travel schedules, work schedule and habits and hours,
Addresses, Changes (History, Current), Reason & When
Background Checks (History, Current) and Changes
Arrests/Judgments (History) and Reasons

TABLE 4

Cybersecurity and Other Relevant Publications

Name & ID
Affiliation (e.g., University, Research Laboratory/Institute, Government (Domestic and International), Company, Consultant, etc.)
Addresses, (current, and dates)
Affiliation history
Author(s) Education, Subject and Location (e.g., BS, MS, PhD, post-doctoral, Technicians, etc.)
Authors(s) Domain Expert (or Subject Matter Expert): Computer Science, Network Administration, etc.)
Author(s) Work history
Other Affiliations (e.g., university, professional societies, etc.): current and history
Publication, Conferences, citations, etc.
Research description and results, funding source, study dates, etc.
Recognition, Awards and Patents
Articles from world-wide, recognized and/or and scientific journals, conferences and proceedings from Google-Scholar Library of Congress, IEEE, etc. and other -like publications (Links to cybersecurity professional, and scientist name and ID)
Articles from world-wide, recognized and/or referred sources in cybersecurity
Articles from journals and publications, Military publications, and other applicable journals. Noting, location and/or origin of attack, time of attack, interval of attack, intended targets, conditions and other information
Articles and resources from the internet, expert-curated accounts, and other validated official alerts systems)
Published network vulnerabilities
Metadata of outbreak, social graph of computer virus transmission vector based on location and time, spread of outbreak as function of time
Metadata from monitoring social media and other sources.
Meta-studies (e.g., composed of various smaller studies)

Table 5 represents Cybersecurity Data and Metadata, Intermediate Results, and Output History that can contain all data and metadata derived from Tables 1-5 inputs and Table 6 outputs and their respective history for use in each cybersecurity application processed. Each cybersecurity application processed can have its own unique Table 8. The information contained in each cybersecurity Table 5 can be used for model building, forensic analyses, trending, change detection, statistical inference and/or prediction based on NLM clustering and adjudication. An entity is a set of attributes (something belonging to an attack, response, alert, etc. and/or groups of these, etc.) defining a point in multi-dimensional space.

TABLE 5

Prior Run Archive

Current Cybersecurity Processing Run (0) ID
Run (0) Time/Date Stamp
Run (0) Input Data
Run (0) Graphical Information
Run (0) Metadata
Run (0) Intermediate Results
Run (0) Output Results
Run(0) Definition of Entity Universe axes and associated attributes
Run (0) Representation of all entities within the entity universe
. . .
Prior Processing Run ID (M)
Prior Processing Run results Table 6 represents an example of cybersecurity outputs that can be used to block, slow down, and/or alert administrators and/or users which is derived from the cybersecurity input Tables 1-5 defined herein. Throughout Table 6, attributes, entities, groups of entities and/or sub-entities, as well as time and location can be utilized in further analysis and/or to refine decisions. The cybersecurity outputs can be provided to network administrators. Network administrators can also include Corporate Information Officers (or equivalent), users, other companies, cyber researchers, government (domestic and international), etc.

TABLE 6

Cybersecurity Outputs

Detected attacking or suspicious IP addresses and recommend an action to address.
Detected attacking or suspicious IP ports and recommend an action to address.
Detected attacking or suspicious software processes and recommend an action to address . . .
Detected attacking or suspicious fraudulent VPN use and recommend an action to address.
Detected attacking or suspicious removable media activity, included unauthorized use, as well as insertion of potential malware and recommend an action to address.
Detected attacking or suspicious users and recommend an action to address.
Detected attacking or suspicious user activity and recommend an action to address.
Detected attacking or suspicious computer and related activity and recommend an action to address.
Detected attacking or suspicious email sources and recommend an action to address . . .
Detected attacking or suspicious email attachments, as well as suspicious individual or groups of email attachments and related the email source(s) and the IP address(es).
Discover and/or identify weak points and/or vulnerabilities in current network topology (design, hardware and/or software)
Detected attacking or suspicious signature and/or activity in network governance policies and recommend an action to address.

FIG. 2 illustrates an example advanced analytics method 200, in accordance with one or more possible embodiments. The processes in the advanced analytics method 200 can be performed by the system processor 128 and can be categorized into four blocks: data conditioning, clustering, mathematical modeling, and adjudication. The two branches of the advanced analytics method 200 shown can include data conditioning modules 210 and 220, clustering modules 212 and 222, math model modules 214 and 224, local adjudication modules 216 and 226, respectively, and global adjudication module 230. The specific data and processing selected for each block can be controlled within a processing branch (intra-branch) by the local adjudication module 216 and 226 and across processing branches (inter-branch) by the global adjudication module 230. The combination of local adjudication modules 216 and 226 addressing the branches and operating in conjunction or separately with the global adjudication module 230 is referred to the adjudication process throughout this document. All input to the system processor 128, intermediate outputs from each processing module and final information from current and prior processing can be placed in the system processor storage 340 (FIG. 3). The advanced analytics method 200 can be implemented in a highly parallel architecture, such that any and/or all of these techniques can be performed serially or simultaneously in parallel on any individual data set, any group of selected data sets and all data sets in any combination.

The processing flow of the advanced analytics method 200, shown in FIG. 2, can be performed by the system processor 128. The individual blocks of the system processor 128 can be partitioned between and operate simultaneously in, one or more of the following implementations: local computing, mobile computing, distributed computing, cloud-based computing, Graphics Processing Unit (GPU), array processing, Field Programmable Gate Arrays (FPGA), tensor processor, Application Specific Integrated Circuits (ASIC), quantum computing, as a software program, and any combination of these computing environments (e.g. where a computer has one or more GPUs, tensor processor, etc. operating as processing accelerators), or another implementation that allows for simultaneous operation of individual blocks of the system processor 128. For example, the system processor 128 and/or the system controller 126 can operate as an "app" on a tablet or smart phone. In at least one embodiment, the system controller 126 and the system processor 128 can be combined into a single computational unit.

The CSP 105 can operate as a distributed system. The analysis of relevant social media and network policy and other relevant cybersecurity publications can also be done in a central or common location and the processed feature vectors (entities) provided to each instance and/or installation of a CSSS 100. Although this processing can be performed in each individual CSP 105, a central or common facility can provide more thorough scanning external sources of information, including published network vulnerabilities, analysis of cybersecurity publications, network policy, etc. A central facility or offline capability can provide a rapid response capability to analyze a new cybersecurity threat with dedicated computer/processing resources.

The user/organizational information could also be analyzed in a central location. This information can be anonymized to meet privacy concerns, but can use a larger statistical sample across all instances of the CSSS 100 to improve the accuracy in defining the insider threats feature vectors.

The use of this tight coupling of processes together with both local and global adjudication processes performed by the local adjudication modules 216 and 226, and global adjudication module 230, respectively, provide several advantages. This coupling can produce a tractable representation to support analysis that makes the best use and optimization of all data.

The implementation and architecture of the system processor 128 is easily extensible and highly scalable through parallelization and can allow all proprietary and/or private data/information to be segregated from other data/information within the system processor 128. The proprietary and/or private data/information can be isolated during processing by the system processor 128 without affecting any other data and/or information. Selected information can be encrypted and/or randomized.

Depending upon the condition of the retrieved dataset, that is if the retrieved data needs to be conditioned prior to processing by the clustering modules 212 and 222 the data conditioning modules 210 and 220 can formulate the entity by performing preprocessing, text processing, data compression, data reduction, dimensional reduction, etc. from the retrieved dataset. The data conditioning modules 210 and 220 can process the data from Tables 1 through 6 as data sources that can be applicable to the CSP 105. In an alternate embodiment, the entity can be formulated in advance of, instead of immediately before, being used by the respective clustering modules 212 and 222. In at least one embodiment, this advanced entity can be formulated with a processing unit outside of the CSSS 100, distinct from the data conditioning modules 210 and 220. Examples of data types can include, but are not limited to, text, alphanumeric, sequences as well as metadata for images, charts, tables, symbols, maps, locations (physical, IP, etc.), graphics, video, etc. The system can accommodate new sources of cybersecurity data as they becomes available using the same processing techniques. The data conditioning modules 210 and 220 can accept analytics inputs data sets A and B, respectively where data sets A and B can share the same data and can be the same data. The data conditioning modules 210 and 220 can perform the same and/or different data conditioning on the inputs data sets A and B, respectively, and can output conditioned data to the respective clustering modules 212 and 222.

Among other operations, the system processor 128, implementing the data conditioning modules 210 and 220, can unify sensor metadata and databases associating unstructured text information for each. By using a common term space for the entity, unification can produces a congruent representation for entity. Note, any data can be structured text (a sentence, a paragraph, a document, etc.) and unstructured text a word, a formula, a mathematical sequence, combinations of these, etc.).

The data conditioning modules 210 and 220 can perform the following preprocessing operations that include, but are not limited to, data consistency or conformance checks, tag data, data compression, data alignment, and any corrections, modifications, repairs and/or replacements of noisy, missing or out-of-bounds data. The data conditioning can be beneficial to performance and subsequent operation of the system processor 128. Since not all data can be in a numeric format, any alphanumeric, or other input data types can be re-encoded by the data conditioning modules 210 and 220 into a numeric representation. Functions performed by the data conditioning modules 210 and 220, such as corrections, modifications, repairs and/or replacement of missing or out-of-bounds data, can be tagged for subsequent analysis for deviation from the original data. The conditioning performed by the system processor 128 and applied to the input data can include, but is not limited to techniques from statistics, information theory, and pattern recognition, as well as other approaches for filtering imperfect data. Based on the input data, the data conditioning performed by the data conditioning modules 210 and 220 can be selected and controlled by the adjudication modules 216, 226, and 230. In situations where multiple sources are used for web traffic, such as content servers certificates, the preprocessing can separate out the separate sources (even though from a single IP address) and analyze each source independently. This approach can allow valid sources through while blocking, for example, a malicious advertising site.

The CSSS 100 can operate in a real-time mode that can monitor all network traffic in and out of the network firewall 120, LAN traffic in the network switch 130, and wireless traffic in the wireless interface 180. In at least one embodiment, the CSSS 100 can monitor subsamples or time slices of the network traffic in and out of the network firewall 100, LAN traffic in the network switch 130, and wireless traffic in the wireless interface 180.

The switch traffic monitor 155 can analyze at all nominal Open Systems Interconnection (OSI) model layers and/or other equivalent network model abstraction. The OSI layers include the data link, network, transport, session, presentation, and application layers. The physical layer can be monitored for disruptions to a signal (RF, optical, etc.) of the external communications 115, local LAN 135, wireless LAN 183, etc. and by a surveillance system to monitor physical access a network equipment room where the network firewall 120, network switch 130, etc. can be located to provide inputs to Table 1. The data link layer can monitor port usage, medium access control for device access and permission to transmit and monitor logical link control for encapsulated network protocols, error checking, frame synchronization, etc., as well as point-to-point protocol monitored for connection authentication, encryption, and compression. The network layer can monitor packet propagation times, IP addresses, and initial and changes to the Access Control List (ACL), etc. in the network firewall 120. The monitoring of the network layer can be used to monitor IP spoofing and monitor attempts to bypass the ACL. The transport layer can monitor Transmission Control Protocol (TCP), User Datagram Protocol (UDP), and other protocols responsible for establishing a link from an origin to a destination. The CSP 105 can monitor protocols, timing, etc. to detect unusual behavior. The session through transport layers can monitor data for correct session establishment, termination, and synchronization, etc., monitor secure socket layer requests, encryption, protocols, etc., and monitor end user application layer operations such as File Transfer Protocol (FTP), Hypertext Transfer Protocol (HTTP), Post Office Protocol (POP)3, etc., to monitor threat and non-threat behavior in the network firewall 120. Specific examples of many items that can be monitored include content length mismatch, protocol mismatch, fragmentation overlap, etc.

The entity formed from the network traffic can include some or all information from all layers within the OSI model discussed above. Entities can be formed for a specific OSI layer and have other layer information included. As an example, a packet from the network layer (layer 3) can have information that includes information about multiple frames that are used to constitute the packet from a lower layer, while the same information from a higher layer, such as transport layers of TCP/UDP protocol can be included across multiple packets entities.

The CSSS 100 can create a super-entity by combining multiple entities based on a systematically selecting a number of shared characteristics or attributes. A magnitude dimension can be added to the super-entity to indicate the number of individual entities that were used to generate the super-entity. The magnitude dimension can be used as an indicator of importance for the super-entity and can be used to indicate repeated attacks vs. a single event that can be explained as something other than an attack, such as an inadvertent packet corruption. After a super-entity is inserted into the entity universe, the formation of the super-entity can continue and subsequently reinserted into the entity universe as more information is processed, replacing the prior super-entity. The use of super-entities can substantially reduce the computational complexity and processing time of the system processor 128.

Super-entity formation can include combining multiple occurrences of items from the input tables. As an example, an super-entity can be combined from similar types of packets that "ignore" or mask the IP address. This type of super-entity can be used to help identify a coordinated attack from different IP addresses that can otherwise be difficult to detect. In another example, a super-entity can be generated where similar packets have the time of arrival "ignored" or masked to identify a "low and slow" attack on the network. Other items that can be "ignored" or masked include protocol, port number, etc. to form entities that are independent of the ignored parameter. The super-entity formation can also include ignoring or masking any combination of attributes that form the super-entity. The CSP 105 can maintain multiple instances of the entity universe operating in parallel where one or more dimensions of the original entity universe are masked or not used. Entities, sub-entities, and super-entities (sub-entity are subsequently defined) can be used for all subsequent processing (clustering through adjudication) in the CSP 105. Throughout the description herein, entities, sub-entities, and super-entities can be used interchangeably.

In the CSSS 100 real-time mode, the CSSS 100 can directly insert the entity into the entity universe based on the magnitude of each dimensional attribute and/or weighted and combined attribute dimension. Entities that are inserted into cybersecurity threat hyper-volumes, can cause a recommended action to address the particular cybersecurity threat. This method of direct insertion of the entity into the entity universe in the real-time mode can substantially reduce the time to determine a cybersecurity threat vs. performing the detailed analysis mode. There can be a small decrease in accuracy for identifying cybersecurity threats in the real-time mode as compared to the detailed analysis mode. Therefore, the system processor 128 can trade processing accuracy for processing complexity and speed.

The data condition modules 210 and 220 can perform text processing that can include Term Frequency-Inverse Document Frequency (TF.IDF), Syntactic, and Sematic processing. Each are discussed subsequently in more detail. Text Processing techniques can be used for all text based inputs, including communications, as well as lower OSI level alphanumeric representations of protocols, port numbers, packet time-of-flight and jitter, etc. The data condition modules 210 and 220 can perform a feature extraction technique that can be used in text processing to improve the speed of performance and convergence of the clustering. For example, text processing (structured and unstructured) can include Information Theoretic (e.g., the TF.IDF), Syntactic and Semantic processing associated with all retrieved datasets and/or a combination of these (each method is subsequently discussed). These techniques can be used with text based documents associated with user and institutional data, social media, network policy and cybersecurity related publications. The data condition modules 210 and 220 can perform other techniques that can also be used to numerically encode such text, such as distributional semantics (e.g. distance between terms, etc.), latent semantic, computational linguistics, indexing, text mining, statistical semantics, Principal Component Analysis and Factoring, histogram generation, etc. In an example, the system processor 128 can formulate the entity using text processing including performing at least one of Information Theoretic, semantic, and syntactic, the entity formulation can include extracting numerically encoded text features from at least one of bulk text, structured text and unstructured text. The system processor 128 can perform the text processing to eliminate at least one unproductive attribute and at least one unproductive entity in nonproductive regions of an entity universe using a loss function.

The data conditioning modules 210 and 220 can use information theoretic, syntactic and/or semantic processing methods. These methods can be used independently, in parallel, in series or in combination to reduce the dimensionally of a high dimensional vector space under the control of the multistage adjudication described herein. At least one embodiment uses Term Frequency, Inverse Document Frequency (TF.IDF) methodology and multiple pairwise Cosine Distances between documents and between entities to extract numerically encoded text features from bulk text, structured text, unstructured text of the retrieved dataset. The Cosine Distance (vector dot product between documents or entities) is a measure of similarity between two term vectors that measures the cosine of the angle between them and can be used to drive the attraction/repulsion in the clustering process. The text processing can be used to identify an individual, individual writing style, programming style, region of origin, etc.

The data condition modules 210 and 220 can perform the TF.IDF process that can generate or modify term vectors formed in the data conditioning modules 210 and 220, with the TF.IDF being a metric that assigns numerical values to unstructured text. A term vector can be a multidimensional vector of alphanumeric features (where terms are the dimensional axis) that represent a document. The data condition modules 210 and 220 can numerically encode these term vectors using the TF.IDF. Document sources, such as all documents that make up a document corpus for the retrieved dataset, can be, e.g., newspapers, magazines, journals, government documents, social media, wiki's, blogs, and/or any other textual sources. TF.IDF can be grammar and/or language agnostic, and can be applied to text in any language, without requiring that the text be translated. The construction of TF.IDF scores and structures, can operate the same for all text in any written language, whether alphabetic (e.g., American English) or iconographic (e.g., Traditional Chinese). Even artificial term spaces, such as chat speak ("lol", etc.), hash tags (#prom), and emoticons (e.g., smiley face) can be utilized in the TF.IDF processing. The data condition modules 210 and 220 can compute the TF.IDF across the document corpus by counting terms in a document, counting the number of documents in the document corpus, and counting the number of documents for a given term, generating a TF.IDF score. The TF.IDF score can be then calculated from these terms. The TF.IDF scores for all terms can be log-normalized for ease of use. When documents are added or removed from the document corpus, the data condition modules 210 and 220 can update the term scores by only adjusting the frequencies for the affected terms. The data condition modules 210 and 220 can perform matching using keywords, sequences, formulas, etc. from queries, profiles, recommendations, and histories.

The system processor 128 need not use all the terms associated with the document corpus to determine a term scores. By sorting the TF.IDF term scores within the corpus of documents, the system processor 128 can perform a match on only the "best" terms within the corpus, that is those having the highest TF.IDF use. The selected terms can be the most sensitive and discriminating terms across the corpus of documents, thus giving both high sensitivity and specificity (each defined subsequently) to later processing.

The system processor 128 can use the TF.IDF processing to generate a term vector for a document based on the term score of each selected term associated with the document. Terms can be space-delimited character strings (words), but other term definitions can include phrases, numbers, names, etc. Measuring similarity between two documents based on their respective term vectors can be done in several ways, as discussed subsequently. It is important to note that not all terms in a document will convey the same amount of information.

A set of all terms that occur anywhere in any document can be represented by the equation $W=\{w_1, w_2, \ldots, w_L\}$ with $T_i(w_j)$ being equal to a number of times term $w_j$ occurs in document i. From this, the system processor 128 can determine the total number of times a term occurs, counting multiplicities, in the entire document corpus D by adding the occurrences in each document.

The data condition modules 210 and 220 can use one or more of a commonly used set of strategies for selecting terms that can include document distance and similarly which disregards grammar, instead regarding each document as a collection of terms. These collections are routinely called "Bags of Words", and the strategies "Bag of Word" strategies. Examples of such strategies can include:

| | |
|---|---|
| Strategy 1 | Documents i and j are similar if, and only if they both contain all of the terms (selected term list). |
| Strategy 2 | Documents i and j are similar if each contains at least N of the terms in a given selected term list, where N is an adjustable parameter. |

The stringent match criterion of Strategy 1 will generally give few false alarms, but will also miss many similar documents. Strategy 1 is specific, but not sensitive. The looser match criterion of Strategy 2 will generally recognize similar documents (along with generating many false alarms). Strategy 2 is sensitive, but not specific. A selected term is "good" for characterizing document content if that document uses the term multiple times. This is because a term that a document uses frequently is likely to be related to what the document is actually about. This makes the match more sensitive to those documents most likely to be relevant. The adjustable parameter, N, can be limited as increasing N provides marginal improvement of document to document sensitivity and specificity. Since the number of selected terms defines the dimensionality of the term vectors, a limit on N can be an initial process in limiting the dimensionality in the cybersecurity processing.

A selected term can also be "good" for characterizing document content if it occurs in most documents that are relevant to a specific concept, condition, and/or entity, but it does not occur in documents concerning unrelated topics. This will enable the selected terms to be used to detect and ignore irrelevant documents, making the match more specific (sensitivity). The perfect selected term(s) for characterizing a document would occur many times in that document, and nowhere else (specificity). This is achieved by combining two sub-metrics: one for sensitivity, and one for specificity.

A good match term $w_j$ for a document $d_i$ will have a large TF and a small DF. TF and DF can be combined into a single metric by taking a ratio where the "large=good" sub-metric TF is in the numerator, and the "small=good" sub-metric DF is in the denominator. To avoid carrying around a complex quotient of fractions, the quotient can be a product of TF with the reciprocal of DF, referred to herein as the Inverse Document Frequency (IDF). A term's IDF value can be quite a bit larger than its TF values.

$$\text{Total count of occurences of term } w_i = \sum_{k=1}^{M} T_k(w_i)$$

is larger than its TF values. Because of this, the logarithm of DF can be taken as an alternate approach to control its magnitude so that it doesn't "overwhelm" TF, resulting in the equation as follows:

$$\log(IDF) = \log\left(\frac{M}{DocCount(w_j)}\right)$$

Since there is no need to compute DF for terms that do not occur in any document in D, $DocCount(w_j)$ will always be at least 1. The TF.IDF term score can be defined as:

$$TF \cdot IDF_{i,j} = (TF(w_j, d_i))(IDF(w_j)) = TF(w_j, d_i)\log\left(\frac{M}{DocCount(w_j)}\right)$$

To measure a keyword's sensitivity to a specific document, the system processor 128 can proportion all occurrences of a term that are in that one document. This can be referred to as the Term Frequency (TF) for that term and document and is defined below. The Term Frequency for term j in document i can be:

$$TF_{ij} = \frac{T_i(w_j)}{\sum_{k=1}^{M} T_k(w_j)}$$

In other words, $TF_{ij}$=# of times $w_j$ appears in document i/# of times wj appears in all documents.

The Term Frequency is a real number between 0 and 1 inclusive, and is zero for documents in which the term does not occur. If there are lots of documents, TF will be a very small number for most terms and a larger number for rare terms. If a term occurs in only one document, its TF will be 1 for that document, and 0 for all other documents.

In at least one embodiment, the TF.IDF processing can apply Synonym Annotation (i.e. using a single common term for synonyms) and making our terms that are of little value such as articles, adverbs, conjunctions, interjections, etc., to documents to accelerate the TF.IDF processing. This process can be used for dimensionality reduction for the term vectors. The Synonym Annotation can be used to accelerate genetic sequence processing.

Prior to TF.IDF processing, the data condition modules 210 and 220 can mask out any terms that occur in many documents that do not provide significant discrimination for any particular topic. Examples of these terms are:

| Parts of speech that are usually poor choices as match terms | |
|---|---|
| Part of Speech | Examples |
| Adverbs | quickly, as |
| Articles | a, an, the |

-continued

Parts of speech that are usually poor choices as match terms

| Part of Speech | Examples |
| --- | --- |
| Conjunctions | and, but, however |
| Interjections | hooray, ouch |
| Prepositions | on, over, beside |
| Pronouns | she, you, us |

These are related to the notion of "stop-words", that are poor stand-alone search terms.

The specificity of a matching term for a corpus D of documents measures whether the occurrence of that term is concentrated in a small percentage of the documents, or found in many of the documents. The Specificity can be computed as the proportion of all documents that contain the term.

Specificity can be represented as follows:

$A(w_1, d_i) = 1$ if term $w_j$ occurs in document $d_j$, 0 if it does not

The total number of documents among the M documents in $D = \{d_1, d_2, \ldots, d_M\}$ that contain term $w_j$ is then given by:

$$DocCount(w_j) = \sum_{k=1}^{M} A(w_j, d_i)$$

Then, the proportion of all documents that contain the term is given by the Document Frequency (DF) for $w_j$:

$$DF(w_j) = \frac{DocCount(w_j)}{M}$$

The Document Frequency is a real number between 0 and 1, inclusive. If the Document Frequency is one, the term occurs in every document. It will be a smaller number (that is less than 1) for terms that occur in fewer documents. If a term occurs in NO document, its DF will be 0 for all documents.

The entity universe can have thousands of dimensions (e.g., a dimension can be a single attribute, a weighted attribute, a summation of weighted attributes, etc.). The system processor 128 can select the dimensionality of the embedding space, the number of dimensions input and/or the number of dimensions output, as a basis for trading accuracy for computational efficiency with the goal of minimizing the number of dimensions used in subsequent processing by the system processor 128.

Ambiguity can measure the comprehension of language and sequences using context and/or structure. Ambiguity can include local and global structures and components of sequences, which follow known and/or discoverable rules. Local ambiguity of can persist for short periods of time and/or short sequences of structured text, unstructured text and/or alphanumeric sequences. Global ambiguity of can persist for long periods of time and/or long sequences of structured text, unstructured text and/or alphanumeric sequences.

The system processor 128 can perform syntactic processing that can measure local and global components of ambiguity, their length, their repartition interval/distance, their group repartition interval/distance and the sequence structures and/or rules of construction, respectively. Syntactic processing architectures can include serial and/or parallel processing. Serial processing tries to interprets the structure of a given text and/or sequence considering one interpretation at a time independently. Parallel processing tries to interprets the multiple structure and meaning of texts and/or sequences and to rank order these interpretations. Syntactic process can include many models, such as Garden path model, Minimal attachment, Constraint-based, and Computational modeling, etc. To facilitate dimension reduction and feature synthesis, each raw sparse vector of terms can be segmented into syntactic blocks (groups of terms having similar form [e.g., tables] or type [e.g., different languages, emoji's, chat-speak]), and/or into semantic blocks: groups of terms having similar function or meaning, e.g., emotive terms, technical terms, etc. Each of the raw text vector segments can be synthesized/encoded into a relatively small number of numeric scores.

The data condition modules 210 and 220 can perform other semantic processing methods independently, in parallel, in series or in combination to reduce the dimensionally of a high dimensional vector space under the control of the multistage adjudication. In at least one embodiment, semantic processing names are not used explicitly but rather semantic context can be used to implicitly define meaning. Ambiguity can measure the comprehension of terms, sequences and alphanumeric sequences. The use of semantic processing can be used to identify artifacts within sequences. These artifacts can be caused by noise, measurement errors, missing data, changes in nominal use, changes in typing patterns, word choice, etc., and/or a combination of these.

The data condition modules 210 and 220 can form intermediate vectors on an original unaltered term vector, can be generated by subdividing term vectors, can be generated by combining one or more weighted term vectors, or can be a combination of these. The weighting of the term vectors to generate the intermediate vectors can be determined in the adjudication modules 216, 226, and 230. The adjudication modules 216, 226, and 230 can determine feature vectors by combining multiple intermediate vectors that represent an entity. An example of combining multiple intermediate vectors can be using separately processed social media text analysis of hacker forums and previously identified cybersecurity threat entities, to improve identification of new network threats.

In addition, the adjudication modules 216, 226, and 230 can generate feature vectors, whether from one or multiple intermediate vectors, by appending parametric data dimensions. This appended information can include information and/or attributes, and/or derived information and/or attributes information contained in the cybersecurity Tables 1 through 6 and can increase the dimensionally of the feature vector as compared to the intermediate vector. This appended information can be conditioned using other methods and techniques previously discussed in this disclosure or can be used as is. The creation of the feature vectors can be controlled by the adjudication process described herein.

The adjudication modules 216, 226, and 230 can tag and generate a feature vector by adding one or more tags to the feature vector. A tag can be numeric, alphabetic, alphanumeric tags, and/or symbolic. The tag(s) can be used to provide a map to the original information source and/or indicate that the feature vector was limited, synthesized, or in some way altered in the data preprocessing. Note tags can be used for privacy and/or randomization and/or represent encrypted information.

Feature vectors (tagged or untagged) can define the set of entities that are used in subsequent processing. Attributes can be considered characteristics that are used in the definition of an entity. Attributes (or unit vectors that span the multidimensional space) can define the entity universe axes. Weighted attributes can be combined to form new dimensionality unit vectors under control of the adjudication process described herein. Throughout the rest of the processing, the feature vectors are referred as entities in the universe. The feature vectors may be unaltered term vectors, intermediate vectors, and/or feature vectors with appended parametric data. In addition, that feature vectors may be tagged or untagged.

The data conditioning modules 210 and 220 can perform dimensionality reduction to simplify subsequent processing with minimal acceptable loss of information contained in the data. Also, the dimensionality reduction can 1) compress/combine attributes, 2) can weight attributes, 3) eliminate regions of the entity universe containing sparse feature vectors, cybersecurity data (e.g., IP address, port number, process, etc.) is often high dimensional but sparse, and/or 4) masked, unmasked, and/or combinations of masked and unmasked attributes. The dimensionality reduction can be done with term vectors, intermediate vectors, and/or feature vectors. An example of dimensionality reduction can be used with low, slow network attacks that done from a large plurality of IP addresses. In this case, the source IP address range can be masked in using the feature vector that represents a network attack vector to compare it to other attack vectors.

Dimensionally of the vector space can be reduced/increased using information loss/gain as a controlling factor. The information loss using Principle Component Analysis (PCA), Singular Value Decomposition (SVD) and/or State Vector Machine (SVM). Also, dimension reduction can be calculated by comparing the mutual information of the high dimension vector space, X, to the lower dimension vector space, Y, I(Y;X)=H(X)−H(X|Y), where H(X) is the entropy of X and H(X|Y) can be considered as the variance loss. This approach can be generalized, that is, if Y explains the variance of X, the mutual information increases and/or decreases. Therefore, mutual information can be used to explain variance. This embodiment can allow the use of all aspects of entropy in the context of mutual information to calculate information loss and gain. The data conditioning module 210 and 220 can reduce the number of dimensions by compressing and mapping P feature vectors onto an S dimensional term vector-space (e.g., where S can be less than P). The multistage, iterative adjudication structure/architecture can select and control dimension reduction via the local adjudication modules 216 and 226. In at least one embodiment, the information loss using PCA, SVC, and/or SVD dimension reduction can be controlled by minimizing loss function (defined subsequently) in the adjudication process described herein. Other methods for reducing the dimensionality of the term vector can include the loss function, expected loss, and/or neural networks. These methods are discussed in the clustering and adjudication processing. In an example, the system processor 128 can performs adjudication to minimize the loss function in order to optimize assignment of the entity by adjusting a decision boundary of the cybersecurity threat hyper-volume.

The data conditioning modules 210 and 220 can perform pruning using text processing to eliminate unproductive attributes and entities in nonproductive regions of the universe using loss function. The data conditioning modules 210 and 220 can use any and all of these techniques in combination.

Calculating metric distances and vector angles in a high dimension space to discern useful information can fail using traditional clustering techniques due to the sparse data that cause ineffectiveness and inefficiency. The data conditioning modules 210 and 220 can perform dimensionality reduction of a very high dimensional vector space with the minimum loss of information under control of the local adjudication modules 216 and 226.

The system processor 128 can perform, in the data conditioning modules 210 and 220, attribute and/or feature vector weighting under control of the adjudication modules, 216, 226, and 230. The feature vector (and attribute) modification can include masking and/or weighting, adding a constant, multiplying by a constant, a unit axis, such as an attribute or combination of attributes. The vector weighting can be controlled by the adjudication process described herein. Note, each dimension of a vector can be weighted separately. Note, the feature processing, dimensionality reduction, and weighting can be performed by the system processor 128 in any order.

In an example embodiment, in which Document i and Document j can characterize some combination of text, sequences, etc. Examples of a term k can be a word, phrase, etc. Documents i and j can include an individual's history, related cybersecurity publications, etc.

The affinity expression, $D^2(i,j)$, can be composed of at least one of Information Theoretic (e.g., TF.IDF), Syntactic, and Semantic terms. These terms can be used independently, in parallel, in series or in combination. The affinity expression can be considered a distance. Note that distance is used interchangeably in this specification with metric and metric distance and/or cosine distance.

The affinity between Document i and Document j can be defined by the exemplary equation as follows:

$$D^2(i, j) = \left\{ \sum_{k=1}^{Terms} [TF \cdot IDF(i, k) - TF \cdot IDF(j, k)]^2 \right\} + $$
(Information Theoretic Term)

$$\{\tau(i) - \tau(j)\}^2 + \{\upsilon(i) - \upsilon(j)\}^2$$
(Syntactic Term) + (Semantic Term)

where:
TF.IDF (i, k)=TF.IDF score of term k within Document i
TF.IDF (j, k)=TF.IDF score of term k within Document j
$\tau(i)$=average word count of the posts within Document i
$\tau(j)$=average word count of the posts within Document j
$\upsilon(i)$=average nuance of the terms within Document i; and
$\upsilon(j)$=average nuance of the terms within Document j.

The individual components, Information Theoretic, (e.g. TF.IDF, bag of words, distance between words, etc.), Syntactic, and Semantic terms can be separately weighted. The $D^2(i,j)$ values can be used to drive the entity attraction and repulsion in the clustering process (subsequently defined). In an example embodiment, the use of computational linguistics, that is, TF.IDF and clustering, and can include linear clustering, nonlinear clustering, linear manifold clustering and/or nonlinear manifold clustering can be applied by the system processor 128 to the available sensor and database information. Manifold clustering can use either a linear or nonlinear manifold with at least one of linear and nonlinear clustering of data embedded on a manifold. This querying can be performed using natural language. A query or group of queries can be treated as a document and processed using the term processing and the linear, nonlinear, linear manifold clustering and/or nonlinear manifold clustering. Using the concept of "nearness", or a small metric distance between entities, also referred to herein as affinity, similarity, and closeness, new decisions can be made in the adjudication modules 216, 226, and 230. These identified entities can be used to create new, more effective and/or less costly decisions boundaries. The concept of "distant" (also referred to herein as dissimilar, not like, and other synonyms of distant) can also be used to eliminate or rank lower decisions. The $D^2(i,j)$ values can be used as a direct input to neural processing in the math model modules 214 and 224.

A cosine distance, using the TF.IDF method, can be a measure of similarity between documents and/or entities retrieved by the system controller 126. This cosine distance metric can be treated as a measure of angular distance between the entities and/or documents being described. For example, if two entities are "near" each other in terms of space defined by TF.IDF, the entities are more likely to be similar than dissimilar.

Information Theoretic (e.g., TF.IDF), Syntactic and Semantic processing by the system processor 128 can be used to analyze the structures of network attack vectors, etc., from the relevant cybersecurity publications.

Term features (e.g. metadata) associated with sensors, and databases and other cybersecurity application textual corpus (e.g., user social media, cybersecurity research, etc.) can include those drawn from bulk text from online sources, published articles, wiki's, blogs, social media content, etc. Information can be drawn by the system processor 128, through the system controller 126, from these sources to enrich the representation of entities.

The CSSS 100 can operate with a distributed computer virus and malware scanning as part of the local computer process monitor 165 and report full and real-time scan results to the CSP 105.

Attributes or combinations of attributes can be weighted, masked, and/or combined to highlight one or more dimensional axes to enhance cybersecurity threat decisions, e.g., website access from a given counter, access from a VPN service, user susceptibility to blackmail or bribe, etc. The weighting, masking and/or combination of these can be controlled by the adjudication modules 216, 226 and 230.

The clustering modules 212 and 222 can perform clustering, visualization, and data seeding functions. The clustering modules 212 and 222 can take the data received from the data conditioning modules 210 and 220, respectively, and output processed data to the math model modules 214 and 224, respectively. The clustering modules 212 and 222 can perform different types of linear, nonlinear, linear manifold and nonmanifold clustering for use in the math processing modules 214 and 224 and adjudication modules 216, 226, and 230. Multiple implementations for forming the linear, nonlinear, linear manifold, and/or nonlinear manifold clusters can include tensor analysis, vector analysis, differential geometry, and spectral analysis. For example, in at least one embodiment vector analysis can be employed. Types of linear, nonlinear, and nonlinear manifold clustering can include linear classifier, nonlinear clustering, nonlinear manifold clustering, nearest neighbor classifier, fuzzy clustering, K-means clustering, K-profile clustering, spectral clustering, neural networks and Nonlinear Dimension Reduction (NLDR) methods, etc. NLDR methods can be used in Riemannian manifold learning.

The linear manifold (LM) clustering can use locally linear and/or locally nonlinear high-dimensional spaces that are embedded on a linear manifold. The nonlinear manifold (NLM) clustering can use locally linear and/or locally nonlinear high-dimensional spaces that are embedded on a nonlinear manifold. Various implementations of nonlinear manifolds can be utilized for multidimensional nonlinear manifold clustering on at least one element of the retrieved dataset, assignment of an entity into a cybersecurity threat hyper-volume based on the multidimensional nonlinear manifold clustering, and determination of the recommendation of cybersecurity action for the system based on the assignment of the entity into the cybersecurity threat hyper-volume.

The nonlinear manifold clustering can improve the probability of detection of the similarities and differences within a given data set while reducing the probability of false alarm by using locally linear and/or locally nonlinear high-dimensional spaces that are connected via a nonlinear manifold. That is, nonlinear manifold clustering allows for a reduction of a highly nonlinear problem to a set of locally linear and/or nonlinear decision regions.

In an example, the utilization of the multidimensional nonlinear manifold clustering further includes utilizing the multidimensional nonlinear manifold clustering and at least one other type of multidimensional clustering including at least one of linear clustering, linear manifold clustering, and nonlinear clustering.

The system processor 128 can derive a set of conformed, that is mathematically well behaved, feature vectors in an N-dimensional Euclidean space, which can be viewed as a Hilbert Space, called the embedding space, from the input data in Tables 1 through 6, and any subset and/or combination thereof. Within the embedding space, each point represents a particular entity and a cluster of points represent an aggregate of entities. Entities can be processed with any manner of linear and nonlinear clustering, as well as linear manifold clustering and nonlinear manifold clustering in the embedding space where the clusters can have any dimension of N or less than N. The use of this embedded space to reduce dimensionality can provide more accurate cybersecurity threat decisions.

The adjudication process performed by the local adjudication modules 216 and 226, and global adjudication module 230 can monitor the cluster development as additional data sources and data types are added to and pruned from the clustering inputs. The local and global adjudication processes performed by the local adjudication modules 216 and 226, and global adjudication module 230 can further prune the linear, nonlinear, linear manifold, and/or NLM clustering that can lead to nonproductive regions of multidimensional spaces being eliminated from consideration for a particular cybersecurity cybersecurity threat hyper-volume. In addition, these regions of the entity universe can be highlighted for future investigations by a domain expert. Feature vector tags can be preserved during the clustering process. Thus, the tags can allow the feature vectors (entities), to be traced back to their original information source through all processing modules. The clustering modules 212 and 222 can further perform manifold clustering, to replace Local Linear Embedding (LLE) and/or ISOMAP techniques (L-ISOMAP, C-ISOMAP, etc.), which can be vulnerable to metric error.

Dimensional weights and metric distance weights can be time dependent. For example, the system processor 128 can apply such time dependent dimensional weights and metric distance weights to the metric distance between threats and non-threats. That is, selected dimensions can use time varying weights to move any combination of entities and/or clusters of entities closer to or further from one another, as a function of time and/or depending on the changing entity and/or varying attributes. These time dependent weights can be used, as an example, to highlight suspicious activity at times when hackers may feel that networks are not being closely monitored. Also, cluster formation and associated cybersecurity threat hyper-volumes can be a function of time. In at least one embodiment, the attraction and/or repulsion between entities and/or centroids of clusters of entities can be controlled by the cost of a decision and/or a function of time.

The clustering modules 212 and 222 can use Monte Carlo insertion to initially place an entity into the entity universe and then use entity attraction/repulsion in the clustering processing to observe the trajectory of the placed entity. The system processor 128 can use Monte Carlo insertion of entities (one or more) to randomly place them into the entity universe and can use entity attraction/repulsion in the process and can use regular relaxation of prior entity insertions and to allow them to reach a positional equilibrium, that is where all forces are balanced, in the entity universe. The system processor 128 can place the entity into an entity universe based on Monte Carlo insertion (including inserting the entity at the same location as the direct insertion) with or without measure of importance. This process can continue until all entities have been inserted into the entity universe. The attraction and repulsion can impact the location of entities previously inserted into the entity universe. The entity-entity attraction or repulsion can be calculated by the system processor 128 based either on the similarity or dissimilarity of the entity-entity pair. In at least one embodiment, the system processor 128 can directly insert the entity into the entity universe based on its attributes. The inserted entity (Monte Carlo method or directly) that fall outside of previously defined cybersecurity threat hyper-volume(s). Any Monte Carlo and/or directly inserted entity not falling inside a previously defined cybersecurity threat hyper-volume(s) can be recommended to be blocked, isolate, delayed/slowed, or allowed, and the user and/or system administrator can be alerted, etc.

In at least one embodiment, the clustering modules 212 and 222 can use Monte Carlo insertion with a measure of importance to place the entity into one or more selected cybersecurity threat hyper-volumes within the entity universe and then use the entity attraction/repulsion in the clustering processing to observe the trajectory of the placed entity until positional equilibrium is reached. The measure of importance for an entity can be used to select a cybersecurity threat hyper-volume, which contains the highest number of shared attributes and weighted attributes with the placed entity. This approach can reduce the amount of processing performed by the system processor 128 required for entity placement. Also, this embodiment can be used with data seeding.

The linear, nonlinear, linear manifold and/or nonlinear manifold clustering can be performed with the clustering modules 212 and 222 to form a set of local metrics for specific cybersecurity decision problems facilitating the use of many tools and methods. In particular, weighted metrics and differential geometry can be utilized by the clustering modules 212 and 222 as one such tool to develop user decisions. Other tools can include spectral theory and functional analysis.

The weighted metrics can indicate a formal metric and/or a pseudo metric. The formal metric can satisfy Euclidean geometry. The pseudo metric can approximately satisfy conditions for the metric since the decision solution can be a numerical result. The weight selection for the metric can be determined by the information content and/or importance of each entity. The weights can be determined during the process of solving the partial differential equation, as described, constructed, and illustrated below.

$\mathcal{F}$ can be a collection of finite length character strings, sequences or feature vectors (e.g., entities):

$$\mathcal{F} = \{A_j\} = \{A_1, A_2, \ldots, A_M\}$$

$d_{ij}(A_i, A_j) = d_{ij}$ can be the metric on $\mathcal{F}$. A distance matrix can be formed as follows:

$$D(A_i, A_j) = [d_{ij}], \; i,j = 1, 2, \ldots, M$$

This distance matrix is symmetric, zero diagonal, non-negative where:

$$S = \{\vec{a_j}\} = \{\vec{a_1}, \vec{a_2}, \ldots, \vec{a_M}\} \in \mathbb{R}^N$$

can be a (hypothetical) set of vectors having distance matrix D. Regarding the $\vec{a_j}$ as a field source, we can define a discrete scalar potential $\wp$ on S by:

$$\wp(\vec{a_i}) = g \sum_{j=1}^{M} (\|\vec{a_i} - \vec{a_j}\| - d_{ij})^2 \quad (*)$$

where g can be a weighting or multiplier on affinity and is a non-negative constant that can be chosen arbitrarily to facilitate sensitivity analysis to determine a cost associated with a decision. The field can allow both the attraction and repulsion of entities in the field, and their positions/distances relative to one another, based on similarities and dissimilarities, respectively. The field can allow the nonlinear manifold to be constructed and allow for measurement of metrics and subsequent determination of decision(s) and confidence regions. The field and its construction are described below.

In general, the existence of such an S for a given D is not guaranteed; in particular, D might not exist for N=1, but exist for N=2. Also, because S is informed only by the distances between the $\vec{a_j}$, any rigid placement of a solution is also a solution. Therefore, a solution can be registered in $\mathbb{R}^N$ for convenience. An approximate solution S for (*) can be found by various methods that include, for example, Singular Value Decomposition, Gradient Descent, and/or Monte-Carlo with or without the measure of importance.

A formal gradient:

$$\wp(\vec{a_1}) = C(\vec{a_1})$$

can define a vector field on, and that is precisely the set of zeros of the Laplacian of (which is to be expected). The field equations can give rise to a radially symmetric scalar potential that are used to drive the cluster formation. The cluster formation can be governed by entity data using the field equation. The closeness of entities and/or clusters of entities can provide decisions for a given cybersecurity decision. The details of this process are described below.

In addition, the linear and/or nonlinear clustering can be mapped (that is, embedded) onto at least one of linear manifold and nonlinear manifold with the clustering modules 212 and 222. The linear and/or nonlinear manifold distance or metric is the relative distance between feature vectors on the linear manifold and/or nonlinear manifold, respectively. The metric provides the relative affinity between feature vectors in the linear, nonlinear, linear manifold and/or nonlinear manifold spaces. The feature tags can then be used to reference the encoded feature vectors back to the original source input(s) and to follow the trajectory of selected entities within the entity universe. The reference metric can be used to indicate the affinity between the various entities described herein for the cybersecurity threats and/or recommended actions addressed.

A field can be defined as the sum of all attraction and repulsion forces of entities for each point in the entity universe. Each entity can have different attraction and repulsion forces in each dimension. Adding and/or subtracting entities to and/or from the entity universe can change or modify the field either locally (within a region) and/or globally (over an entire universe). Also, fields can be based on multidimensional feature vectors that can be arbitrarily defined (e.g., a directly inserted entity and/or a seeded entity). The field can consist of many dimensions and can change with time and/or with the addition (or deletion) of new (or existing) entities. The field can be classified as scalar, vector, tensor, statistical (many body), etc. Note, the method described of cluster formation using physical and/or mathematical constructs of attraction and repulsion can be controlled by the adjudication process described herein.

The "field" can govern the cluster formation used for generating the linear clustering, nonlinear clustering, linear manifold clustering and/or nonlinear manifold clustering. The field controls the placement of entities (data from at least one database, including information of at least one entity with cybersecurity databases and sensors metadata) into the linear, nonlinear, linear manifold and/or nonlinear manifold cluster formation. In addition, the placement of additional entities in an existing field can modify that field (that is, can create a new field). The entities can both attract/repel other entities within the clustering process based on the defined field. The field can satisfy a superposition principle, so additional entities can be directly placed in the existing space. A cybersecurity cybersecurity threat hyper-volume can have a its own unique governing field based on contained entities. The field can be conservative. In particular, the field can be path-independent, not needing to retain the history to understand their immediate effect on the field. The entity universe and the interaction of all entities can be a mathematical construct that can be arbitrarily defined, including differing magnitudes, the fall-off or increase of force as a function of distance (r, 1/r, 1/r^2, or any other mathematical construct), time varying, with and/or without attraction/repulsion interaction between selected entities, or a combination of all three of these constructs. These force fields can be between entities or clusters of entities and/or combination of these. Different force fields can be applied to different entities and different multidimensional regions under the control of the local and global adjudication module 216, 226 and 230, respectively. Entities in the entity universe mathematical construct are not bound by physical constraints and can occupy the same position at the same time and move through other entities without disrupting the position of the entities until the positional equilibrium of the entity universe is reached (if so desired).

The resulting linear clustering, linear manifold clustering, nonlinear clustering, and/or non-linear manifold clustering, performed by the system processor 128, can be embedded in a Hilbert Space of appropriate dimension that creates coordinates in a natural way using unsupervised machine learning. The Delta Rule is a first-order gradient descent method. When the Delta Rule is written as a distance minimization expression, the Delta Rule can be a differential equation describing a vector field. A gradient descent solution (to place the data within a multidimensional coordinate space) can then be a set of Lagrangian Points (stable point or location within the multidimensional field where the forces are in equilibrium), which can satisfy this differential equation. In at least one embodiment, the Hamiltonian formulation can be used. In this way, the field is an emergent property of the entity position, with the positions constrained by the mutual forces of attraction and repulsion. The dimensionality of the space can be selected by the system processor 128 to minimize error, and a machine-learning theory variant of the Delta Rule can be used to perform the clustering (of cybersecurity sensor metadata and data, etc., and any combination thereof including subsets of the clusters). An energy function can be calculated from the solution of the differential equation. The energy function can provide a measure of how efficient/complete the clustering is to minimize the energy of the resulting field and allow the clustering to reach positional equilibrium. The formed cluster can correspond to a surface of minimum energy as defined by a partial differential equation of order 1 or greater. The concept of minimum energy ensures an optimum solution for a decision and/or recommended action that can be achieved.

Other methods can be used to develop a distance matrix from the input data contained within the formed clusters, such as Singular Value Decomposition, Lagrange Multipliers, Newton's Method, or any other method that can construct a coordinate system from the data. In at least one embodiment, an adaptive convergence can be used where the attraction and repulsion is accentuated initially and then lessened as convergence of the cluster formation is reached to speed up the processing. In at least one embodiment, simulated annealing can be employed to halt the cluster formation processing after a fixed amount of time. The adaptive convergence and simulated annealing can be used in conjunction with each other. The adaptive convergence and simulated annealing can be performed in the math modules 214 and 224.

The system processor 128 can formulate and apply a weighted metric to entities. In at least one embodiment, this weighted metric can be a single weighted metric. The unification can allow the system processor 128 to uniformly treat entities in one or more dimensional spaces. From this single weighted metric, the system processor 128 can formulate an objective function which can drive the linear, linear manifold, nonlinear, and non-linear clustering. In this way, the cluster formation can be recursive, and adaptive (i.e., depending on the data). Other metrics can be created and applied to related data representations. For example, the system processor 128 can cluster entities. The objective function can be used to derive an Nth-order partial differential equation, for example, having the form of Laplace's Equation, the properties of which can characterize the linear, linear manifold, nonlinear, and non-linear clustering. In particular, properties of Laplace's Equation can allow data points, data dimensions, and data classifications to be added, removed, and modified without having to reconstruct the entire linear, linear manifold, nonlinear, or nonlinear clustering. The Laplace Equation, together with the use of weights in the metric, can be used by the system processor 128 to apply a unified representation to several operations without requiring data refactoring, such as:

1) clustering of entities including the interaction of previous cybersecurity decisions;

2) clustering of cybersecurity entities data;

3) clustering of any combination and/or aggregation of entities data in the same, unified space; and 4) computation of numeric measures of vector distances or metrics between any and all of the above in the various unified spaces that can be used by the local 216 and 226 and global 230 adjudication modules.

The use of distances can include Euclidian, Riemann Manifold, other Nonlinear Manifold distances, etc.

The system processor 128 can divide entities into two or more sub-entities. An entity can be divided into two or more sub-entities if the source information generating the feature vector for the entity is conflicting and/or sets the entity in a position that underlying information is negated or masked. At least one embodiment of this process can analyze the individual source term vectors, etc. for the entity and separate the entity into a set of two or more sub-entities if the mean and/or variance (i.e., statistical moments) is above a threshold. Throughout this disclosure, the use of the term sub-entity can be substituted for entity with regards to functionality. In at least one embodiment, the Monte Carlo technique and direct insertion, with or without the measure of importance, can be used to discover stable points for selected entities placed in the entity universe. Multiple entity stable points can be used to create the sub-entities. Stable points can exist where an entity and/or groups of entities are in positional equilibrium.

The clustering modules 212 and 222 can use an N-Dimensional visualization engine to compute and display descriptive statistics for the data, for example, minimum, maximum, range, standard deviation, mean, and/or histograms for entity population subsets. Automatic clustering (Autocluster Capability) may be selected to automatically group data into a domain expert-determined number of clusters based upon the relative distribution of data. The N-Dimensional visualization engine can be extensible by the addition of analytic tools such as a Feature Analyzer (Bayesian), Principal Component Analysis (PCA) (Karhunen-Loeve), and classifiers (Likelihood ratio, expert system, Radial Basis Function, Multi-Layer Perceptrons, rule inducers, etc.). Using a visualization process performed by the clustering modules 212 and 222 can allow for a domain expert to view the results of the linear, nonlinear, linear manifold, and/or NLM clusters' development in real-time or near real-time, allowing the domain expert to make adjustments or tuning the cluster formation process to test certain hypotheses. Visualization can be utilized for the training process.

The advanced analytics method 200 performed by the system processor 128 can generate an array of N-dimensional visualization engines that allow domain experts to view, manipulate, and analyze sets of discrete data points in high dimensionality, simultaneously. These visualization engines can make use of one or more of color encoding, position encoding, cluster and neighborhood encoding, and time encoding using frame-by-frame capturing of information in a video format, including virtual and/or augmented reality. Visualizing time and the clustering of disparate data in this way allows the viewing of the temporal formation, evolution, and disintegration of data features. Examples of this timing and clustering visualization can be the likelihood of a network attack or intrusion with an indication of criticality, the likelihood of process corruption or malware with an indication of criticality, the likelihood of an insider attack with an indication of criticality, etc.

The advanced analytics method 200, performed by the system processor 128, can implement system commands that can allow selection of any number of sets or subsets of the data contained in Tables 1 through 6 by entities, sub-entities, super-entities, attributes, and/or characteristics, in various manual approaches (Select Capability). A control device, such as a mouse and/or keyboard, can be used to select subsets of data on the display device by enclosing them (e.g., Lasso Capability, etc.). Data subsets can be merged to create new subsets (Combine Capability); subsets can be disbanded (Clear Aggregates Capability). The domain expert can subsample the population (Sampling Capability) and mask out undesired data fields (Feature Projection Capability). These manipulations need only be done in detailed analysis mode and/or early training and stored for future reference as domain expert preferences and/or workflows, after which the advanced analytics method 200 can be automated based on the stored domain expert preferences and/or workflows. These training techniques can be considered a subset of machine learning. The system controller 126 can be used to retrieve the data from any of Tables 1 through 6. Thereafter, the system processor 128 can use the retrieved data to formulate a retrieved dataset as a basis to generate an entity.

Data seeding can be performed during the clustering process performed by the clustering modules 212 and 222. Data seeding can force the multidimensional-clustering around designated regions of the multidimensional space (sometimes referred to herein as the hyper-volume). This seeding can highlight entities and/or clusters of entities with common attributes within a hyper-volume containing the seed. Known, suspected, and/or conjectured network attack vectors, insider threats, etc. can be used for data seeding. The system processor 128 can identify an entity and/or cluster of entities containing a distinct set of attributes that are similar, that is close to the seeding attributes. Such data seeding together with multiple math models performed by the math model modules 214 and 224 and the adjudication process performed by the local adjudication modules 216 and 226 and global adjudication module 230 can highlight similar entities. Seeding forces the multidimensional-clustering around designated regions of interest. Note, the seed can be an entity that is defined by a user or the system processor 128.

In addition, seeding can be performed to direct cluster formation (defined subsequently) in certain locations within the multidimensional space. The seeding can be either weighted or unweighted. Similarly, masking can be used to filter entities from an existing cluster. Seeding can also be used in the adjudication process in conjunction with the math model modules 214 and 224 to measure confidence in the decisions (subsequently defined.)

The math model modules 214 and 224 can perform predictive analysis, statistical analysis, statistical inference, tracking, etc. on the conditioned data received from the data conditioning modules 210 and 220 or entities and/or feature vectors from the clustering modules 212 and 222 and/or in conjunction with the local adjudication modules 216 and 226 and global adjudication module 230. The mathematical model performed by the math model modules 214 and 224 can use multiple models to focus on the high pay-off regions within the linear, nonlinear, linear manifold and/or nonlinear manifold clustering processes. Output from each math model can be input into the adjudication process performed by the local adjudication modules 216 and 226 and the global adjudication module 230 and selected output can be used. The advanced analytics method 200 can use multiple models, including statistical models and deterministic models. These models can be applied to one or more of the embodiments disclosed.

Calculated with each statistical model is a confidence region or confidence interval. These models and confidence regions can be applied to all processing modules, e.g., data conditioning 210 and 220, clustering 212 and 222, local adjudication 214 and 224 and global adjudication 230. The calculations that can be performed in these math model modules 214 and 224 are disclosed as being used elsewhere in this application. Examples of these calculations include regression analysis, pattern recognition, Kalman Filtering, Maximum Likelihood Estimation, all statistical calculations, all metric distance and all angle calculations, and all vector and tensor operations.

Also, statistical analysis, statistical inference, prediction, tracking, change detection, event detection and mathematical modeling can be performed in the math processor modules 214 and 224. Examples of these mathematical modeling can include statistical moments (centroids, means, variances, skewness, kurtosis, etc.), single and/or multiple linear and/or nonlinear regression, Maximum Likelihood Estimation (MLE), Bayesian calculations or any other mathematical modeling that allow for determination of decisions and confidences, by the system processor 128. For the tracking of trajectories over time and/or the ingestion (deletion) of new (old) information, Autoregressive (AR) models, polynomial fit, splines, and Kalman Filtering, etc. can be utilized by the system processor 128, which can provide useful properties in a space and can compensate and/or predict changing, evolving and/or emerging patterns, sequences and/or structures in the data and/or metadata of cybersecurity threat decisions and recommended actions.

The mean of a cluster of entities or an aggregate and/or subset thereof can be represented by a centroid of that cluster in the N-dimensional attribute space (that is, the entity universe and/or a selected hyper-volume within the entity universe). For example, the centroid of a cluster of entities can be used to define a representative entity for that cluster.

The clustering modules 212 and 222 input selected data and output their results to the math model modules 214 and 224 to calculate applicable uniqueness measures, vector-space metric distances, inverse metric distances, cluster centroid and other cluster statistical moments, thresholds, term and feature vector weights and/or masks, metric distance weights, the minimization of a loss function, and the Bayesian decision quantities (e.g., likelihood functions, posterior predictive utility distribution of the vector x, and the expected loss (EL) under the predictive distribution). Note, the hyper-volume and associated boundary enclosing that hyper-volume can be calculated as well.

Using the techniques of information geometry, signature extraction, and building classifiers, etc., can be performed in the math model module 214 and 224.

Math models developed by the CSP 105 can be used to identify and predict new relationships that can exist outside known and/or suspected attack vectors and/or training datasets. For example, math models can identify and/or predict a developing attack vector and/or an insider attack.

The $L_k$ norm can measure the metric distance between any combination between entities and/or the centroid of entity clusters, etc. to establish decisions according to:

$$L_k(x,y) = \Sigma_{i=1}^{d}(\|x^i - y^i\|^k)^{1/k}, \text{ where } x, y \in R^d, k \in Z$$

Where d is the number of dimensions in the entity universe.

In an example, $L_k$ norm with k smaller than 1 (that is, fractional) can be more effective at preserving the meaningfulness of metric distance in a high dimensional space. Many high dimensional algorithms use a Euclidian metric distance (k=2 defined below) as an extension to its traditional use in two-dimensions and three-dimensions. In at least one embodiment, the $L_k$ norm (defined below) can be k=1 (Manhattan Metric Distance) or other values of k.

In other embodiments, the following metric distances can be used to determine a Pearson Correlation distance, Absolute Pearson correlation distance, Un-centered Correlation distance (same as Pearson Correlation distance with sample means set to zero), Absolute, Un-centered Correlation distance, and Kendall's (tau) distance (for nonparametric distance measurements).

Individual dimensions (i.e., attributes, weighted attributes, weighted combinations of attributes, masked attributes, etc.) within resultant linear, nonlinear, linear manifold and/or NLM clusters can be weighted to accentuate or diminish the importance of selected attributes. In addition, inter-cluster or inter-entity vector distances can be weighted to accentuate or diminish the relative sameness or difference of the clusters or entities. Furthermore, the NLM clustering process disclosed herein can increase the effective data signal-to-noise-ratio (DSNR) to improve detection of weak correlations between entities/attributes. The CSP 105 can apply error minimization and linear, nonlinear, linear manifold and/or NLM clusters to cluster assignment techniques to achieve noise reduction. More specifically, these techniques can simultaneously and systematically minimize errors while maximizing detection of cybersecurity threats in the clustering process and entity to cluster hyper-volume assignments.

The angular distance, "$A_k$" and the metric distance, $L_k(x, y)$ can be used in the adjudication process described herein.

The angular measure, A, between two vectors, x and y (including a centroid(s)), in a high dimension vector space can be calculated using a normalized dot product of two vectors:

$$A_k = \cos^{-1}(x \cdot y / L_k(x, y))$$

An entity can consist of data/metadata from Tables 1 through 6 or any combination (e.g., internet usage, individual profile, cybersecurity research, social media, etc.). Some examples of metrics are a norm of a vector difference and a norm of a weighted vector difference. If required, the math model modules 214 and 224 can calculate all angles between multidimensional vectors between all entities or groups of entities.

A hyper-volume can be constructed within the entity universe (along a vector originating from an entity and/or centroid of a cluster of entities associated with a previous entity assignment to another entity and/or centroid of a cluster of entities using metrics and/or angles offset from that vector. This process can be repeatedly performed for each decision and used in the multistage iterative adjudication. This procedure can be used to include a new entity into an existing cybersecurity threat hyper-volume and can transfer the attributes of that hyper-volume to the new entity. In addition, the new entity can replace the cluster with a summation of the attraction and repulsion of all the entities in the cluster and the new entity can be used in the attraction and repulsion calculations instead of the individual entities in the cluster. This approach can radically simplify and speed up the attraction and repulsion processing.

The distance metrics and vector angles can be combined to calculate and track trajectories of the entity, statistical moments, etc. (e.g., as a function of time) in the math modeling modules 214 and 224 under the control of the adjudication process performed by local adjudication 216 and 226. Regression analysis, Auto Regressive (AR), Auto Regression Moving Average (ARMA), Maximum Likelihood Estimation, or Kalman Filtering can be used to predict and track this trajectory, and predict changes to decision boundaries. The use of these techniques can detect the number of entities/attributes and/or the rate of change of entities/attributes as a function of time for visualization of activities that can indicate the likelihood of a network attack or intrusion and its criticality, the likelihood of process corruption or malware and its criticality, the likelihood of an insider attack and its criticality, etc. or any other attribute derived from the information contained in the tables. Subsequent processing iterations can be selected and controlled by the local and global adjudication processing modules 216, 226, and 230 based on rules and associated actions and based on the output from the math model modules 214 and 224.

The math model modules 214 and 224 can use a covariance matric to construct confidence regions and sensitivities. This sensitivity matrix can be used to model the sensitivity of quantities to variations in parameters (e.g., time). Many math modeling methods (e.g., regression, AR, MLE, Kalman Filtering, etc.) are available for use with the disclosed embodiments.

Adjudication can be performed using the local (intra-branch) adjudication modules 216 and 226 and/or the global (inter-branch) adjudication module 230. For clarity in further discussions, a branch refers to a single set of processing modules 206 and 208 with the local adjudication module 216 operating only with modules 210 to 214 and inter-branch refers to operating across all branch processing chains in which the global adjudication module 230 interacts with the local adjudication modules 216 and 226. This two-stage adjudication is discussed for simplicity. In at least one embodiment, multistage adjudication can include any number of stages and any feed forward and/or feedback stage interconnections. The various interconnects illustrated in FIG. 2 can be bi-directional. And, in an example at least one or more global adjudication modules 230 can exist and connect to a super global adjudication module (not shown).

Multistage adjudication control can include (1) control of processing dataset flow and routing among branch modules 206 and 208 and across branch modules 206 and 208, (2) control of algorithm selection and associated processing parameters in branch modules (e.g., type of clustering, dimension reduction techniques, etc.), and/or (3) control of a number of iterations through given branch modules based on the risk function (subsequently defined), cost function (defined subsequently), error and/or the loss function (subsequently defined), which can minimize the risk and/or cost of a wrong recommendation of an action being made and/or minimize the risk/cost of a valid recommendation of an action not being made.

The local adjudication modules 216 and 226 can select decision cost functions (e.g. quadratic, absolute value, etc.). This decision cost function can be used to measure elasticity and/or sensitivity in the decision process. For example, in the cybersecurity, the decision cost function can be a decision cost to a block or slow down an individual, a lock out a user, etc., or a combination of these.

The advanced analytics method 200 can use an adjudication process performed by the local adjudication modules 216 and 226 to systematically select the best decisions (e.g., minimizing loss/cost/error) produced by branch modules 206 and 208 for a given entity and/or group of entities. The adjudication process, performed by the local adjudication modules 216 and 226, allows the objective and principled application of mathematics and knowledge to render a summary assessment by fusing information from Tables 1 through 6 and produce reports giving insight into the reasoning system behind the system processor 128 conclusions.

The global adjudicator 230 can use branch decisions, and apply principled analytic techniques and knowledge to produce a fused product that is generally "better" than any of the single branch decision alone (subsequently defined). Decisions can be used to discover relations, processes, events and/or highlight overt and obscure structures, patterns and information using principled analytic techniques, as well as prediction and confidence region using cluster parameters, decision regions (hyper-volumes and boundaries) and/or entity assignments.

Iterations can be performed and compared in the adjudication modules 216 and 226 for use in pruning of nonproductive data, nonproductive processing branches, in conjunction with math modeling modules 214 and 224 computations, etc. Local adjudication 216 and 226 can use a set of rules, as examples, to control the selection and masking of source data, data conditioning, cluster formation, math models, and adjudication methods, etc. throughout the branch processing. The global adjudication module 230 can also feedback control and data via the bidirectional global adjudication feedback bus 244 and 254 function in which results and control are fed back to the previous local adjudication modules 216 and 226. The local adjudication modules 216 and 226 can also control feedback functions in which results (e.g. metadata, results, etc.) can be fed back to prior processing modules. The local adjudication modules 216 and 226 can feedback control and data via the local adjudication feedback bus 242 and 252 to the data conditioning modules 210 and 220, the clustering modules 212 and 222, the math model modules 214 and 224, respectively.

A decision boundary can be a threshold, a multidimensional surface enclosing a threat decision/discovery region or hyper-volume. The surface can be defined as containing the hyper-volume, that can include a null set(s), an entity or groups of entities and/or entity clusters, that separates that hyper-volume from the remaining entity universe. Note: a separate cybersecurity threat hyper-volume can exist within a larger hyper-volume or partially overalap another hyper-volume. The ability to separate hyper-volumes within larger hyper-volumes or partially overlapped hyper-volumes is critical to identify threats that can "hide" within non-threats.

All relevant entities and entity clusters can be defined by a set of attributes, including weighted attributes, combinations of weighted attributes, masked attributes, etc. Recommendations can be generated in the system processor 128 and transmitted from the system controller 126 to a UE 110 for presentation to a user, such as via a local display, a web interface, augmented/virtual reality, and/or other human-computer interface.

The adjudication performed by the system processor 128 can include statistical decision processing, neural network processing, or a combination of these. The system processor 128 can generate decisions/reasoning that can be presented to the user in a rank ordered lists based on confidence regions generated in the math modeling modules 214 and 224. Information can be combined in two or more entities by forming a derived entity by combining the attributes. The derived entity can be then processed as a standard entity.

The system processor 128 can make optimal decisions under uncertainty of outcomes using statistical decisions. One way of addressing uncertainty can use probabilistic and statistical reasoning. A common method of this is Bayesian decisions coupled with expected utility maximization, discussed herein. Decision support systems have been developed for various applications. These systems can be passive vs. active, individual vs. collaborative, non-Bayesian vs. Bayesian, and Parametric Bayesian vs. Non-Parametric Bayesian. All of these systems or combination thereof (called hybrid filtering) can be used with the system processor 128 described herein.

The system processor 128 can balance two types of errors. Type I error is a false positive. Type II error is a false negative. A decision threshold can be established to balance Type I and Type II errors using a decision cost function. Examples of cost functions can include monetary loss, risk, loss of reputation, etc. (or combinations thereof) for cybersecurity. The calculation of Type I and Type II errors can be performed in the math processing modules 214 and 224 and the balancing of the Type I and II errors can be under the control of the adjudication modules 216, 226 and 230. Type III error is a result of making the correct decision for the wrong question. Each error type can have an associated cost and/or loss functions. Note, if required, the system processor 128 can use other higher order error types. Note, in cybersecurity threat detection, the terms sensitivity, that is, the true positive rate or the probability of detection, and specificity, that is the true negative rate, can be used. Sensitivity can quantify avoiding false negatives and specificity can quantify avoiding false positives. Therefore, the system processor 128 can convert and present error types in user jargon for greater understanding.

The system processor 128 can make statistical decisions that can be used to manage uncertainty by minimizing the expected loss and/or cost of a wrong decision, for example, failure to stop a network attack, disrupting a valid user from completing a valid task, etc. At least one embodiment can use a Maximum Likelihood Estimator. Also, embodiments can use at least one of different probability distributions, for example, Gaussian, Uniform, Binomial, Poisson, Exponential, and any other probability density functions that can provide for managed uncertainty.

A loss function can be used to minimize the cost, risk and/or error of decisions. Examples of loss functions are regret, quadratic, 0-1, absolute value, etc. In the case where the loss function is a random variable, Frequentist and Bayesian expected loss can be calculated. In at least one embodiment described herein, Bayesian expected loss (expected loss and EL(x) are used interchangeably with Bayesian expected loss herein) can be calculated using the loss function $l(x,u)$. The expected loss can also be used to minimize the cost, risk and/or error of decisions. Note, vectors are represented by bold characters. Bayesian decisions use the following definitions: the utility function, u, can be defined by 1) a probability model parameter space M (the probability model can be locally selected), 2) observation data D, 3) an initial or iterative processing pass specified prior $p(M)$ over the model parameter space M and 4) an initial or iterative processing pass probability model $p(u|x, M)$, and can update the posterior over M using Bayes' rule:

$$p(M|D)=[p(D|M)p(M)]/p(D)$$

Where $p(D|M)$ is called the likelihood function. The posterior predictive utility distribution of the vector x is:

$$P(u|x,D)=\int_M p(u|x,M)P(M|D)dM$$

In order for the system processor 128 to determine the optimal decision, that is, the best decision, Bayesian decisions can utilize a loss function, which is an overall measure of loss/cost/risk/error incurred in taking any of the available decisions or actions. This loss function, $l(x,u)$, can be defined as the loss incurred by recommending item x when the true utility function is u. Then the Bayesian expected loss for deciding x is defined for both Type I and Type II errors as the expected loss, EL(x), under the predictive distribution given by:

$$EL(x)=\int_u l(x,u)p(u|x,D)du$$

The expected loss can be used in both the local adjudication 216 and 226 and global adjudication 230. The risk function can combine the loss function $l(x,u)$, rules, actions, and the probabilities. More precisely, the risk of a decision is the expected loss with respect to the probabilities $p(u|x, D)$. Other loss function embodiments such as a quadratic loss, squared loss, absolute value loss, etc. can also be used. The quadratic loss function can be used in t-tests, regression models and other statistical methods.

Note: if x is made up of discrete values (instead of continuous values) then the integral can be replaced by a summation. Also, a multi-attribute utility function, $u(x)$, can be defined over a vector x with n dimensions, $\{x_1, \ldots, x_n\}$ using $u(x)=u(x_1, \ldots, x_n)$.

For Bayesian decisions, the optimal item x* that minimizes the expected loss:

$$X^*=\arg\min EL(x), x \in X$$

The x can be used to define the decision boundary(ies) between entities and entity clusters in the multidimensional entity universe.

The expected loss and/or cost for both Type I and Type II errors can be weighted. The weighting can represent the relative loss/cost/risk/error of each type of error (Type I and Type II) and can change the hyper-volume boundary.

This equation represents an optimization with the local adjudication 216 and 226, where an absolute optimum (in this case, the minimum) is determined over all x∈X in each processing branch as shown in FIG. 2. Bayesian optimization can maintain a probabilistic belief and/or disbelief about the expected loss (EL) and based on an acquisition function to determine where to evaluate the function next. Optimization methods are subsequently discussed herein.

The x* represents the decisions presented to the user together with a decision score that can indicate a likelihood that decision is correct. The decision score can be 1) based on the decision confidence (defined subsequently), 2) scaled and/or 3) can work with linear, logarithmic, and/or other compressive scaling techniques. In at least one embodiment, the decision can also be represented by a number of symbols, and/or any other quantitative symbolic representation of accuracy.

The system processor 128 can use many acquisition functions that can be interpreted in the framework of Bayesian decisions, such as evaluating an expected loss, EL(x) at a given point x. This evaluation can produce suboptimal results when the entire entity universe is considered, but an optimal result can exist for a selected multi-dimensional subregion of the entity universe. For some situations, then the suboptimal solution can be the better decision for a particular network attacks, malware detection and prevention, insider attacks, etc. Other embodiments of the acquisition function can include Probability of Improvement, Expected Improvement, Entropy Search and Upper Confidence Bound, etc. For simplicity of explanation, the acquisition function can evaluate the expected loss, EL(x) at a given point x.

The system processor 128 can select the retrieved dataset to ensure an optimum decision. In at least one embodiment, the entity can be weighted and processing methods can be combined to improve the decision process. The adjudication process performed by the local 216 and 226 and global 230 adjudication modules can select optimized weights for the term and feature vectors and weighted metric distances.

An example embodiment of the interaction between the entity selection and processing modules is present here. The local adjudication modules 216 and 226 can observe the output of the math model modules 214 and 224 for a given set of input data and a given set of processing methods, i.e., the data conditioning modules 210 and 220, and clustering modules 212 and 222. This output can include a uniqueness measure, that is an identification of an entity and/or cluster of entities containing a distinct set of same or similar attributes, metric distances, metric distance statistics, and cluster statistics while the adjudication modules 216 and 226 monitor the expected loss. In addition, effects of thresholds/region settings, feature vector and feature vector weights, metric distance weights, and the calculation of the Bayesian decision quantities, for example, the likelihood function, posterior predictive utility distribution of the vector x, can be performed while monitoring the EL(x). The EL(x) can also be used in dimensionality reduction, e.g., reduce the number of attributes, combined attributes, weighted and combined attributes, etc. The local adjudication modules 216 and 226 can include a set of rules and associated actions, and can initiate each of the methods of data conditioning modules 210 and 220, clustering modules 212 and 222, and math processing modules 214 and 224 to minimize the EL(x).

Optimization can be used to find arguments of an EL(x) function which can yield its minimum, that is, looks for a global minimum of the objective function. Note, optimization can minimize the EL(x) objective function and/or maximize the negative of the EL(x) objective function (e.g. reward, etc.). For machine learning cost, EL(x), and/or error objective functions are typically minimized. Such optimization can be performed using numerically, e.g., which can involve guessing, or analytically, e.g., which can involve computing derivatives of the objective function and looking for critical points. This process can continue until the global minimum, i.e., the minimum for the entire objective function, is found. Note, these methods can be performed on multidimensional objective functions.

Optimization can be divided into Convex, that is, without saddle points, and Constrained, that is, optimized over a region and/or set of feasible point. Example of constrained optimization is the Karush-Kuhn-Tucker method using generalized Lagrangian, Gradient verses Non-gradient methods, Gradient Descent, Stochastic Gradient Descent, Simulated Annealing, Nelder-Mead (Simplex or Amoeba), Particle Swarm, Evolutionary Algorithms (Genetic Algorithms, Evolutionary Strategies, Evolutionary Programming), Derivative-Free Optimization, Hessian Optimization, Advanced Algorithms (Conjugate Gradient, BFGS, L-BFGF), etc. Examples of optimization of multidimensional objective functions can also be used with TF.IDF for dimensionality reduction and clustering formation.

The minimum loss function and/or expected loss can be calculated to find the decision boundary and/or boundaries for the selected hyper-volume containing a group of and/or cluster of entities. The gradient decent method can be used to find the optimum decision boundary. This multidimensional decision boundary can be used to select the data, select module processing methods and control the processing for each module or group of modules to minimize the expected loss. The adjudication can minimize a loss function (e.g., expected loss) associated with the optimal assignment of the entity from the multidimensional clustering by adjusting a multidimensional decision boundary of the multidimensional cybersecurity threat hyper-volume.

Uncertainty can exist in any cybersecurity decision process that resides in the system processor 128. There can be multiple embodiments to manage uncertainty and system reasoning. These embodiments can include statistical reasoning, constraint solvers, logic programs, rules engines, deductive classifiers, machine learning systems, case-based reasoning systems, and procedural reasoning systems. In at least one embodiment, the system processor 128 can minimize the Root Mean Square Error (RMSE) across all decision regions to set threshold and/or boundaries. In at least one embodiment, the system processor 128 can minimize the Root Sum Square Error (RSSE) across all decision regions to set threshold and/or boundaries using linear and/or nonlinear regression analysis. In at least one embodiment, the classification can be rule-based systems which are based on selected axiomatic rules, that is, unquestionable rules, such as the blocking access to specific websites.

The selection of clustering, e.g., linear, linear manifold, nonlinear, and nonlinear manifold, methods performed by the system processor 128 and the metric distance statistics and the cluster statistics can be used to determine the similarities and distinctions between entities, clusters of entities and/or a combination of these. The smaller the metric distance is, the greater the affinity or similarity between entities. Correspondingly, the larger the metric distance is, the greater the differences between the entities. In at least one embodiment, the system processor 128 can use the closeness of one entity to another entity to transfer a decision, in whole or in part, to the second entity. In at least one embodiment, multiple decisions thresholds and/or boundaries can be set based on the inverse distance, or inverse metric, and/or the distance, or metric, between an entity cluster centroid, or a defined location in the entity universe, and another entity or entity cluster. Using the metric, closeness can be defined if the metric is less than a threshold. In another example, using the inverse metric, closeness can be defined if the inverse metric is greater than or equal to a threshold. The example embodiment described hereafter uses the inverse metric exceeding, or crossing, a threshold and/or boundary as a basis for determining a decision. In at least one embodiment, multiple decisions thresholds and/or boundaries can be set based on combination or the inverse distance and the angular measure between an entity cluster centroid, or a defined location in the entity universe, and an entity or entity cluster. Using a combination of inverse metric and angular measure, closeness can be defined if the combination is less than a threshold.

Individual entity thresholds and/or boundaries can be optimized using the information contained in cybersecurity Prior Run Archive, using machine learning and based on the probability and cost of a missed decision, that is, missing the opportunity to take an action, and the probability and cost of an erroneous decision, that is, providing misinformation. In at least one embodiment, single and/or multiple linear and/or nonlinear regression, Maximum Likelihood Estimation (MLE) calculations can be used for decisions. The local adjudication modules 216 and 226, and global adjudication module 230 can perform an adjudication process that can establish thresholds and/or boundaries and decisions when these thresholds and/or boundaries are crossed.

In at least one embodiment, the local and global adjudication modules 216, 226, and 230 using Bayesian decision theory can be extended to a game theoretic approach using decision cost. This approach can use knowledge of decision cost of the entities and/or clusters of entities to modify decisions. Bayesian decisions can be formulated for decisions for individual entities and/or clusters of entities. Game theory can be used to formula an optimum decision cost strategy and can build on the intra-branch and inter-branch adjudication multistage structure, previously described.

In at least one embodiment, the local and global adjudication modules 216, 226, and 230 can be implemented using a neural network. Neural network weights, biases, and thresholds can be manually and/or automatically controlled by the local adjudication modules 216 and 226 and the global adjudication module 230. The local adjudication modules 216 and 226 and the global adjudication module 230 can learn and/or train using a training set (subsequently discussed). Various types of neural nodes can be used with the local and global adjudication modules 216, 226 and 230. These nodes include perceptron and the sigmoid neurons, learning/training algorithms, e.g., stochastic gradient decent, recurrent neural networks, multi-layer feed forward network and the multi-layer feedback network, Radical Bias Functions (RBF), Recurrent Neural Networks (RNN), Hopfield Network, Boltzmann Machine, Self-organizing map, Learning vector quantization, Echo State Network (ESN), long short-term memory network, Bidirectional RNN, Stochastic Neural Network, and many Modular Neural network which can include Committee of Machines, and Associative Neural Network.

Cost functions can be incorporated into neural networks and can be similar to the utility function associated with Bayesian decisions discussed herein. For example, the cost function, C, can be the quadratic cost function. This cost function can indicate how good the training is. The aim of training is to minimize the cost function C varying a set of weights and biases using gradient decent method (subsequently defined). Other cost functions can include Cross-Entropy cost, aka, Bernoulli negative log-likelihood and Binary Cross-Entropy, Exponential cost, Hellinger distance, Kullback-Leibler divergence, and Itakura-Saito distance. The use of the cost minimization can measure the effectiveness of the neural network implementation, that is, weights and biases, in solving the decision problem like the statistical decision approach presented previously.

The global adjudication module 230, in conjunction with the local adjudication modules 216 and 226, can perform adjudication that can allow the strength of one component of the decision process to compensate for weaknesses of another process (subsequently defined). The methods of statistical decisions and/or neural networks can be used to perform this multistage adjudication. For simplicity, statistical decisions and neural networks are discussed independently. However, in at least one embodiment both approaches can be applied synergistically in multistage adjudication for decisions in the same adjudication module and/or different adjudication modules. A result of such adjudication allows for optimized use of an available entity, information, processing, and associate processing parameters. And, the local 216 and 226 and global 230 adjudication modules can construct an optimized processing solution for a given cybersecurity problem and associated retrieved and/or the entity by principled selection and control of these datasets and local/global adjudication modules 216, 226, and 230. Additionally, methodology of data selection and data conditioning utilized by the system processor 128 can differ depending on the retrieved and/or the entity used and the math processing modules 214 and 224 modeling used in conjunction with the type of clustering used.

After the expected loss has been minimized by the system processor 128 for each processing branch established by the local adjudication modules 216 and 226, the results from each processing branch can be input into the global adjudication module 230. The global adjudication module 230 can combine one or more processing branches and the entity to create a fused solution for the system processor 128 on an entity-by-entity basis. The global adjudication module 230 can select and control different processing techniques in various regions of the multidimensional decision space. The global adjudication module 230 can direct each local adjudication module 216 and 226 using a unique set of rules to guide and find the global optimum, e.g., gradient descent. This minimization of posterior predictive utility distribution of the vector x can be iterative and performed until an optimized $X^*$ is found and can create an ordered list of decisions and associated decision scores provided to the user device together with the reason for each decision. This list can be transmitted to the UE 110 by the system controller 126. In at least one embodiment, the local and global adjudication modules 216, 226, and 230 can use statistical decisions, neural networks and/or combination of these methods to select input retrieved and/or the entity, select and control branch processing modules, and control processing flow to provide a decision. Statistical decisions and neural networks can be used synergistically using the system processor 128 architecture herein disclosed.

Creating an optimum decision boundary can be defined as follows: 1) Create multidimensional cluster of entities/sub-entities based on attributes and feature vectors using at least one of many linear, linear manifold, nonlinear and nonlinear manifold clustering methods, 2) use at least one of Bayesian Decision and neural network processing to calculate a multidimensional cybersecurity threat hyper-volume and associated decision boundary for each type of clustering to achieve a minimum $EL(x)$ using gradient descent to assign entities (sub-entities) to cybersecurity threat hyper-volumes, and 3) global adjudication can select the lowest expected loss across the clustering methods used as the solution.

In at least one embodiment, the system processor 128 can use the minimum expected loss solution and can assign individual entities to a given cybersecurity threat hyper-volume using the highest decision confidence from each clustering method used. Each entity decision confidence can be calculated based on cluster statistics and/or decision boundaries enclosing said entity and/or cluster of entities, reaches positional equilibrium, or a combination thereof. For cybersecurity applications, the high precision techniques described provide for accurate identification of cyber threats with a lower probability of false alarms. With current cybersecurity systems, the high false alarm rate can either saturate system administrations responsible for network security or cause real threats to be ignored due constant false alarms.

In at least one embodiment, the entity cluster centroids and number of clusters from the selected lowest expected loss adjudication can be used for seeding other non-selected clustering methods to re-perform each non-selected clustering method. The number of clusters can be limited to the same as the selected lowest expected loss method. The individual entities can then be assigned to a given cybersecurity threat hyper-volume using the highest decision confidence from each clustering method used. If an entity is placed, using various clustering methods, into hyper-volumes with different recommended actions, the entity can be analyzed for potential division into sub-entities. In at least one embodiment, the entity cluster centroids, such as location and number, from the selected lowest expected loss adjudication can be used for seeding the other non-selected clustering methods to re-perform each non-selected clustering method. The number of number of clusters within the entity universe can be limited to the same as the selected lowest expected loss method. The individual entities can then be assigned to a given cybersecurity threat hyper-volume by performing a weighted sum derived from each clustering method. The weighting is based on the decision confidence from each respective clustering method.

Any of the decision and/or entity assignment embodiments can be applied regionally to adjacent cybersecurity threat and/or non-threat hyper-volumes sharing a decision boundary(ies). The entity regional universe can use weighted regional optimum entity assignment(s) to produce a regionally more precise decision boundary(ies) for an entity and/or group of entities. Note, this approach can allow more accurate decisions necessary for precise identification of cybersecurity threats. Note, here the posterior predictive utility distribution of the vector x can be minimized for the selected hyper-volume and the enclosed entities. Although the vector x may optimize the loss function to set decision boundaries across the entity universe, within a selected region or selected hyper-volumes the vector x can be optimized locally. Therefore, each selected hyper-volume and/or groups of hyper-volumes in the entity universe can be optimized independently. This can be useful for cybersecurity applications, as an example, to improve cybersecurity threat detection where an attack is purposely disguised as ordinary traffic. Performing a regional optimization can improve separation of threat vs. ordinary behavior. The approach described here can also reduce the required samples and/or convergence time for training for a given cybersecurity threat hyper-volume. Note: a separate cybersecurity threat hyper-volume can also exist within a larger hyper-volume. The ability to separate hyper-volumes within larger hyper-volumes is critical to recommend different levels of a cybersecurity threat recommendation of an action associated with the smaller hyper-volume that can exist within the larger hyper-volume. A cybersecurity threat hyper-volume can be used to recommended a command of block IP address, block access, block process, block port, isolate threat, lockout user, slowdown/delay access, alert the network administrator, alert the user, and/or do not take an action, etc., and the system controller 126 further transmits the recommendation command to be taken in response to a cybersecurity threat to a network equipment, etc. As an example, the threats found in the smaller threat hyper-volume can be blocked while threats in the larger threat hyper-volume can be delayed.

The system processor 128 can assign the threat entity to a second cybersecurity hyper-volume. For example, a threat hyper-volume can be a first hyper-volume. The system processor 128 can assign the threat entity regionally to a second cybersecurity hyper-volume, the first and second cybersecurity hyper-volumes can share a decision boundary with each other. The second cybersecurity hyper-volume can be a threat, non-threat, an indeterminate hyper-volume, and any other type of hyper-volume. These principles also apply equally to non-threat entities and/or indeterminate entities. For example, the system processor 128 can assign a non-threat entity from a non-threat hyper-volume to the second cybersecurity hyper-volume, the first and second cybersecurity hyper-volumes can share a decision boundary with each other. Once re-assigned, the re-assigned entity (e.g., threat, non-threat, indeterminate, etc.) takes on the recommended action of the second cybersecurity hyper-volume. The first and second cybersecurity hyper-volumes can be either overlapping and partially overlapping hyper-volumes.

The system processor 128 can perform any of the embodiments iteratively and can be performed until the optimum entity assignment is achieved. Successive iterations can select the data flow and processing control until the minimum expected loss can be achieved and the optimum assignment of the entity close to a given boundary can be made. Also, the global adjudication module 230 can select the best embodiment and/or combinations of embodiments that optimizes entity assignments (e.g., near a boundary) and minimizes the expected loss for the regional minimization and/or global minimization of posterior predictive utility distribution of the vector x. The global adjudication module 230 can also determine the weighting of results from the different intra-branch processing embodiments and/or combinations of these.

The multistage adjudication performed by the adjudication module(s) 216, 226, and 230 can be trained to identify the cybersecurity threat hyper-volume(s). The adjudication module(s) 216, 226, and 230, while using the loss function to weigh the cost of a network breach vs. the cost of protecting the network, can perform two methods of training learning machines: unsupervised and supervised. Unsupervised training can exclude known results during training. Input data can be grouped (e.g., exclusively) on the basis of its statistical properties and clustering. Supervised training includes both the training data and the desired outcome data. The use of seeding in the case of supervised training can improve the accuracy of the clustering, potentially reduce the size of the training data set, time to train, and can control the bias in the clustering process and can reduce the amount of processing required for training. The construction of a proper training set can maximize decision accuracy, reduce the training set, and minimize selected set bias. A proper training set can be constructed using known results, e.g., a previous network attack, a previous response, conjectured attacks, white hat attacks, insider data breach, insider attack, etc., and/or reserving a portion of the data for training and then using the results of this training set to process the remaining data. The approach described here can also reduce the required supervised training samples and/or convergence time for unsupervised training for a given decision. All prior identified cybersecurity threats from all sources can be used as part of the training data to identify cybersecurity threat hyper-volumes.

The system processor 128 training can use an iterative, multi-mode, math model. Multiple views of the data space can enter a trainer, typically located in the local adjudicator 216 and 226, which can use an adaptive algorithm to infer modeling parameters. These constitute a collection of candidate solutions to the modeling problem which are assessed and calibrated to create a hybrid system for performing adjudication. Results that are ambiguous or have an indeterminant entity assignment can be used to identify areas for further investigation. At least one embodiment can use Artificial Intelligence (AI)/Deep Learning methods in hierarchal adjudication process. AI can be performed by one or more neural networks, statistical methods, and/or computational intelligence.

TABLE 7

Cybersecurity Functional Process Flow

| Process | Description |
|---|---|
| 1 | Select and preprocess data - On subsequent iteration passes, the adjudication controls the selection of data and data preprocessing techniques |
| 2 | The text processing can generate the term vectors from the using Information Theoretic (e.g., TF.IDF), and can perform Syntactic and Semantic processing techniques associated with any and/or all input textual data selected and processed in process 1. |
| 3 | Feature vectors can be generated by summing weighted term vectors from operation 2 and appending additional information that is outside text processing. The feature vectors can then be tagged. |
| 4 | Term, intermediate, and feature vector dimensionality reduction can be controlled by utilizing information loss/gain in the PCA, SVD, and/or SVM processing. The dimensionality reductions can also be controlled by using the Loss function and/or mutual information. |
| 5 | Generate entity universe axes by combining term feature vectors and feature vectors attributes. At this point all dimensions/unit vectors for the cybersecurity application can represent the entity universe (that is, span the multidimensional space).<br>The feature vectors calculated in operation 4 represents the "entity universe" in which data from Tables 1-5 can be incorporated. |
| 6 | The clustering process can use any form of linear, nonlinear clustering, linear manifold clustering, as well as nonlinear manifold clustering. |
| 7 | Data Seeding can be used in the clustering process and/or the adjudication process. |
| 8 | Monte Carlo insertion using entity attraction/repulsion can be used in the clustering process with relaxation.<br>The entity can also be directly inserted the into the entity universe based on its attributes |
| 9 | The system processor can divide entities into sub-entities and reperform the clustering. |
| 10 | Math Processing can calculate metric distances and associated statistical moments, detect changes in the entity universe and prediction. The metric distances of entities (or cluster of entities) to other entities and/or clusters of entities. This can include different $L_K$ norm formulations and the angular $A_K$ "distance", as well as other functions.<br>In at least one embodiment, metrics can use the processing where the system processor 128 highlights an entity, a set of entities (or combination of sets of entities). |
| 11 | Adjudication to control processing: Multistage adjudication control can include (1) control of processing selected retrieved and/or the entity flow and routing among intra-branch processing modules and inter-branch processing modules, and (2) control of algorithm selection and associated processing parameters in all processing modules and/or groups of processing modules as previously defined, and (3) control of a number of iterations through a given processing modules and/or groups of processing modules based on the risk/cost/loss function, cost function, minimizing the decision RMSE and/or RSSE, and/or the loss function, which can minimize the risk and/or cost of a wrong decision and/or minimize the risk/cost of a valid decision not being made. Further description of this process is defined in Table 8.<br>The methods of reasoning, including statistical decisions theory and/or neural networks can be used to perform adjudication. Both approaches can be applied independently and/or synergistically in multistage adjudication for decisions in the same adjudication module and/or different adjudication modules.<br>The adjudication process can be done in parallel or in iterative runs. |

Table 7 can include an example functional process flow for the system processor 128 implementing the various modules illustrated in FIG. 2, as discussed throughout this disclosure. In Table 8 Adjudication and Optimization implementation can use a Bayesian approach, and the role of the domain expert can be defined. Table 8 is included in Table 7, process 11. For example, Table 8 can include example Bayesian adjudication, optimization, and training. Initially, the domain expert can the retrieved datasets, the size of the retrieved and/or the entity, the training method, processing methods, loss/cost/risk choice, entity assignment method and training methodology. The CSP 105 can perform the iterations, decision boundary development, entity assignments and selects the minimum loss function for the entity universe. The CSP 100 can perform the iterations, decision boundary development, entity assignments and selects the minimum loss function for the entity universe. The CSSS 100 can be used to build cybersecurity relevant models by the domain expert. In at least one embodiment, Table 8 Adjudication and Optimization implementation using neural network can be defined, and the role of the domain expert can be defined.

In at least one embodiment, Table 8 Adjudication and Optimization implementation can use one or more Bayesian and/or the neural network approaches for different regions within the solution space, i.e., the entity universe, and the role of the domain expert can be defined. Note, these techniques presented in table 7 and table 8 can be applied to the cybersecurity threat recommendation and the subsequent command described herein, for the detected threat.

TABLE 8

Bayesian Adjudication, Optimization, and Training

| Process | Description |
|---|---|
| 1 | System processor can select data/metadata from one or more Tables. A manageable subset of data/metadata or limited dimensionality (masking) can be used based on initial conditions. |
| 2 | Perform parallel process on same selected data/metadata using different algorithms in each processing module (e.g., different data and data conditioning, different clustering methods, different math models, etc.). This can be done selectively. |
| 3 | Select best combinations or regional segmented combinations from process 2 methods using loss function. (Other methods (e.g., MLE, Kalman Filter, Minimize RMSE, Minimize RSSE, entropy, etc. can be used) |
| 4 | Modify cost function equations for the loss function to set optimum threshold(s) and regions.<br>Observe result of changes using the loss function. Optimum processing strategy minimizes expected loss. For the processing module under test |
| 5 | Based on the loss function and associated utility function and entity/attribute vector freeze the methods in the module under test and vary other modules at least one other module and observe the change in the loss function. |
| 6 | Use global adjudication to select best processing branch. Repeat processes 1 to 5 as required continuing to observe the expect loss processing performed in the math model module |
| 7 | Rate of convergence/divergence, determination of cluster inclusion, bias, etc. as a tool to signal off ramp |
| 8 | Domain Expert can control training process, initial data set and dimensionality, maximum data set and dimensionality, method of expansion of data set and dimensionality, class of cost functions (e.g. cubic, quadratic, etc.), update coefficients for cost functions, thresholds, bias of data, weights and masking, collaborative filtering, etc. |

FIG. 3 illustrates an example system processor 128, in accordance with one or more possible embodiments. The system processor 128 can be configured as an array of computation units with computation units 1-A thru T-A making up a first column of computation units, computation units 1-B thru T-B making up a second column of computation units, computation units 1-C thru T-C making up a third column of computation units, and computation units 1-S thru T-S making up the Sth column of computation units. Computation units 1-A, 1-B, 1-C, and 1-S can make up a first row of computation units, computation units 2-A, 2-B, 2-C, and 2-S can make up a second row of computation units, computation units 3-A, 3-B, 3-C, and 3-S can make up a third row of computation units, and computation units T-A, T-B, T-C, and T-S can make up an Sth row of computation units. The system processor 128 can include, for an example, six horizontal high speed switches 310, 312, 314, and 316 and, for example, five vertical high speed switches 320, 322, 324, 326, and 328. The high speed switches 310, 312, 314, 316, 320, 322, 324, 326, and 328 can facilitate rapid reconfiguration of the array of computation units 1-A thru T-S. This design is data-driven, highly parallel and highly scalable. This disclosure describes the architecture and processing performed in the system processor 128, together with a description of each processing blocks and its interaction with all other processing blocks, as well as the implementation and operation of the decision making performed in the system processor 128. A grouping of a set of computational units can form a computational unit from the computational unit 1-A thru 1-S. Although the example system processor 128 is illustrated as being a T by S processor array, the system processor 128 can be any configuration of any number of processing blocks within rows and columns that optimizes the processing of algorithms discussed herein. All interconnects shown in FIG. 3 can be bi-directional.

FIG. 3 illustrates a parallel implantation of the system processor 128. In at least one embodiment, all calculation can be performed serially and interim calculation results can be stored for use in subsequent operations. The system processor 128 can include a parallel multi-branch architecture that includes vertical crossbar switches 320, 322, 324, 326, and 328. These switches can be controlled via a set of rules from at least one or more local adjudication modules 216 and 226 and at least one or more global adjudication modules 230 in the multi-branch parallel architecture shown. All input information or prior run archives may exist in databases and be input to the system processor 128 and can be stored in the system processor storage 340.

It should be understood that, notwithstanding the particular operations as shown and described in the figures, a variety of additional or different operations can be performed depending upon the embodiment, and one or more of the particular operations can be rearranged, repeated or eliminated entirely depending upon the embodiment. Also, some of the operations performed can be repeated on an ongoing or continuous basis simultaneously while other operations are performed. Furthermore, different operations can be performed by different processing blocks or in a single processing block of the disclosed embodiments. For example, the local adjudication modules 216 and 226 and global adjudication module 230 are shown as separate blocks, other embodiments of the CSP 105 can support adjudication in the data conditioning modules 210 and 220, clustering modules 212 and 222, and math processing modules 214 and 224, and/or any combination. This distributed adjudication architecture can reduce subsequent processing to accelerate the decision method results and optimization of the entity within the its respective hyper-volumes.

A simplified example can demonstrate the operation and value of the CSSS 100 methods and apparatus described herein. The entity universe is multidimensional and can contain threat entities (such as external and internal network attack vectors, insider threats, etc.), and other entities that are generated by non-threats. The system processor 128 can create an entity universe from Tables 1-6 or use a previous or externally generated universe for the detailed analysis mode and/or a combination of these. These techniques presented here can be applied to the cybersecurity threat decision and the subsequent response for the detected threat.

The CSSS 100 can operate in two general modes. The real-time monitor mode (subsequently discussed) can be used constantly monitor ongoing network operations and activity where threats are identified as they are occurring and responses are predetermined from the detailed analysis mode and/or network policy. The detailed analysis mode can be used for identifying the threat hyper-volumes (and/or forensic mode), as well as identifying non-threat hyper-volumes. The detailed analysis mode can examine prior operation (periodically, randomly, or when a threat has occurred or is suspected) of the network and computer use over period of minutes to years to identify new threats, as well as changing threats, prior breaches, etc. that have not been previously detected and/or identified in the real-time operation. The CSP 105 can perform the detailed analysis mode in parallel with the real-time mode. The detailed analysis mode can be done locally or in a central facility. At the completion of the detailed analysis mode, the updated cybersecurity threat hyper-volume generated during the detailed analysis mode processing can be used in the real-time analysis mode to identify real and potential threats. Note, the detailed analysis mode can also be used for supervised and/or unsupervised training.

In both the real-time and detailed analysis modes, the CSP 100 can ingest the network traffic inputs (including internal switch traffic), process monitor inputs, user information, cybersecurity and other relevant publications. social media, etc. to generate entities that are based on this information. In addition, externally generated entities that define threats and non-threats can be utilized. This monitoring can include all network traffic in and out of the network firewall 120, LAN traffic in the switch traffic monitor 155, and wireless traffic in the wireless process monitor 185. The switch traffic monitor 155 and wireless process monitor 185 can analyze at all nominal (OSI) model layers or equivalent models. Specific examples of attacks that can be monitored include content length mismatch, protocol mismatch, fragmentation overlap, etc. These attacks can cause a buffer overflow allowing an attacker to breach transport layer security in an unpatched operating system.

In the detailed analysis mode, the text input, such as cybersecurity publications, social media, network policy, etc. can use the data conditioning modules 210 and 220 preprocessing, text processing (including information theoretic, syntactic, and sematic processing), feature vector selection, dimensionality reduction, and weighting and/or masking to generate entities that can be used to further train the system to identify threat and non-threat hyper-volumes. Entities can be placed into a cybersecurity threat hyper-volume that can trigger a recommended action to address the threat. The recommended action can include disabling the user account, blocking local computer resource access, blocking internet access, etc.

In the detailed analysis mode, the data conditioning modules 210 and 220 can operate on 1) network traffic, 2) the process monitoring, 3) user/organization information, and/or 4) the related cybersecurity publications and social media, etc. For all data sources, the information can be preprocessed to check the data consistency and/or conformance, tag data, data compression, data alignment, and any corrections, modifications, repairs and/or replacements of missing and/or out-of-bounds data.

In the detailed analysis mode, following this process, the information can be textually processed using information theoretic (TF.IDF), syntactic, and semantic methods. The information from the individual specific source can generate attributes and/or intermediate vectors for each data type. The attributes and/or intermediate vectors for each source can be weighted and/or combined into a feature vector that represents threats and non-threats. The cybersecurity publications and research, social media, and network traffic, including file transfers, can be separately textually processed to identify key threat clusters and associated hyper-volumes contained in the entity universe. Each entity can be tagged to provide a link to its original information source and/or indicate that the feature vector was limited, synthesized, or in some way altered in the data preprocessing. Dimensionality reduction in the data conditioning modules 210 and 220 can be performed on the intermediate and/or feature vectors based on a minimal acceptable loss of information. The dimensionality reduction can 1) compress/combine attributes, and the dimension of the entity universe, 2) can weight attributes, and/or 3) eliminate regions of the entity universe containing sparse feature vectors using PCA, SVD, and/or SVM methods. The entities are then passed to the clustering modules 212 and 222 by the data conditioning data conditioning modules 210 and 220, respectively.

In the detailed analysis mode, the clustering modules 212 and 222 can perform linear, nonlinear, linear manifold, and nonlinear manifold clustering. The various forms of clustering can be compared to improve differentiation of entities. Following the clustering, the math model modules 214 and 224 can perform math processing that can estimate the probability distribution for each cluster and can calculate the associated statistical moments for each cluster.

The adjudication modules 216, 226, and 230 can minimize the loss function to create the cybersecurity threat hyper-volume(s) and assign an entity to that cybersecurity threat hyper-volume(s). This assignment can use a utility function and cost of Type I and Type II errors to define the cybersecurity hyper-volume(s) of threats and non-threats. The system processor 128 can use training with supervised learning to improve the assignment of the entity within the cybersecurity hyper-volume(s) that exhibit threat and non-threat behaviors. The adjudication modules 216, 226, and 230 can perform iterative runs to search for network traffic or user interaction sequences that can more accurately identify threat behavior while minimizing the probability of false alarms. The formation of the decision boundaries and can use either the NLM cluster formation standalone or the full adjudication approach to define cybersecurity threat hyper-volume(s) described to identify potential threat behavior in the entity universe.

In the detailed analysis mode, in at least one embodiment, the loss function can use the expected loss. The adjudication process can minimizes the expected loss across the entire entity universe. The expected loss for selected regions (that is, cybersecurity threat hyper-volume(s)) of the entity universe can be processed independently to improve local decision boundaries and entity assignment in that region and to improve accuracy.

In the detailed analysis mode, the iterative runs can mask dimensions or limit large numbers of entities of the entity universe and monitor the impact on the expected loss. The inputs threat behaviors identified from various interim runs that show promise can be subsequently combined to further minimize the expected loss. The CSP 105 can use a gradient descent method to report the findings once further iterations show marginal improvement. The expected result is a set of identified threat hyper-volumes that can be reported to the system administrator for subsequent action, or from which the recommendation command can be generated. The threat, as well as non-threat feature vectors can be combined with the external feature vectors to be used to define the threat hyper-volumes in the real-time threat detection operation of the CSSS 100. In addition, the detailed analysis mode can be used to forensically analyze prior attacks to identify threat hyper-volumes.

In the detailed analysis mode, the system processor 128 can create an entity universe that delineates threat and non-threat hyper-volumes. These hyper-volumes can contain entities that have been generated from network activity, network operations, users, cyber-publications, social media, etc. These attributes can be selected by the adjudication process described herein and can be explored by the system administrators/Subject Matter Expert.

The real-time mode can use the cybersecurity threat/non-threat hyper-volumes identified in the latest or any prior run detailed analysis mode. In the real-time operation, the CSP 105 can use the entities formed in the data conditioning modules 210 and 220 and can insert them directly into the entity universe or use the Monte Carle insertion method. The location of the inserted entity into a hyper-volume that has been identified the detailed analysis mode can trigger a defined recommendation of an action to be taken. If the inserted entity is in a cybersecurity threat hyper-volume that has been identified in the analysis mode as an attack, then the system processor can recommend the appropriate action to block, end a process, lockout a user, etc. Inserted entities (Monte Carlo method or directly) that fall outside of previously defined cybersecurity threat hyper-volumes (indeterminant entities) can be recommended to be blocked, delayed/slowed, or allowed and can also alert the user and/or system administrator, etc. based on network policy. The recommended actions can be implemented in internal equipment or equipment provided by others. Actions can include blocking a specific IP address (internal or external), a specific port, disabling a user account, etc. Entities generated during the real-time mode can also be used as input for the detailed analysis mode.

An example use of the CSSS 100 is to address Spectre and Meltdown malware that uses the speculative execution of modern processors to create a side-channel attack. A failed speculative execution cache interaction is an example of a side-channel attack that can corrupt the cache or allow memory access outside of the allowed privilege projection ring for the executing program. The initial vulnerability was in cloud computing in which malware running on one virtual machine could access the resources across the entire computer. Although the initial Spectre and Meltdown malware occurrences were quickly patched, many subsequent variants have been uncovered with the expectation of many more variants in the future. An anticipated vulnerability is using speculative execution with Java or other web browser language to do the side-channel attack to bypass the processor security that could impact common use.

In at least one embodiment, the CSP 105 can analyze the application layer data flow of a web browser's Java execution code to detect potential side-channel attacks. The data processing modules 210 and 220, can use the information theoretic, syntactic, and sematic techniques to generate entities or super-entities from the executable program that monitor for branch instruction sequences, distance between branch instruction sequences, etc. The entity generation for the Java execution code can also include the lower level OSI layer, such as IP addresses, port number, etc. If an entity generated from the application layer monitoring, when inserted or reinserted into the entity universe, falls in an identified cybersecurity threat hyper-volume, a recommended action can be taken to stop or minimize the threat. The cybersecurity threat hyper-volume can be identified by analyzing prior side channel attacks in training. The approach can be a direct mode of identifying a cybersecurity threat. Indirect detection can be detected by monitoring for aberrant behavior. Once the indirect behavior is detected, the detailed analysis mode can iteratively use a snapshot of the event history to ferret out the specific cybersecurity attack by isolating processes and programs on the computer where the side-channel attack occurred. Note, any OSI model layer or equivalent can be analyzed in the above manner.

Figure 4:
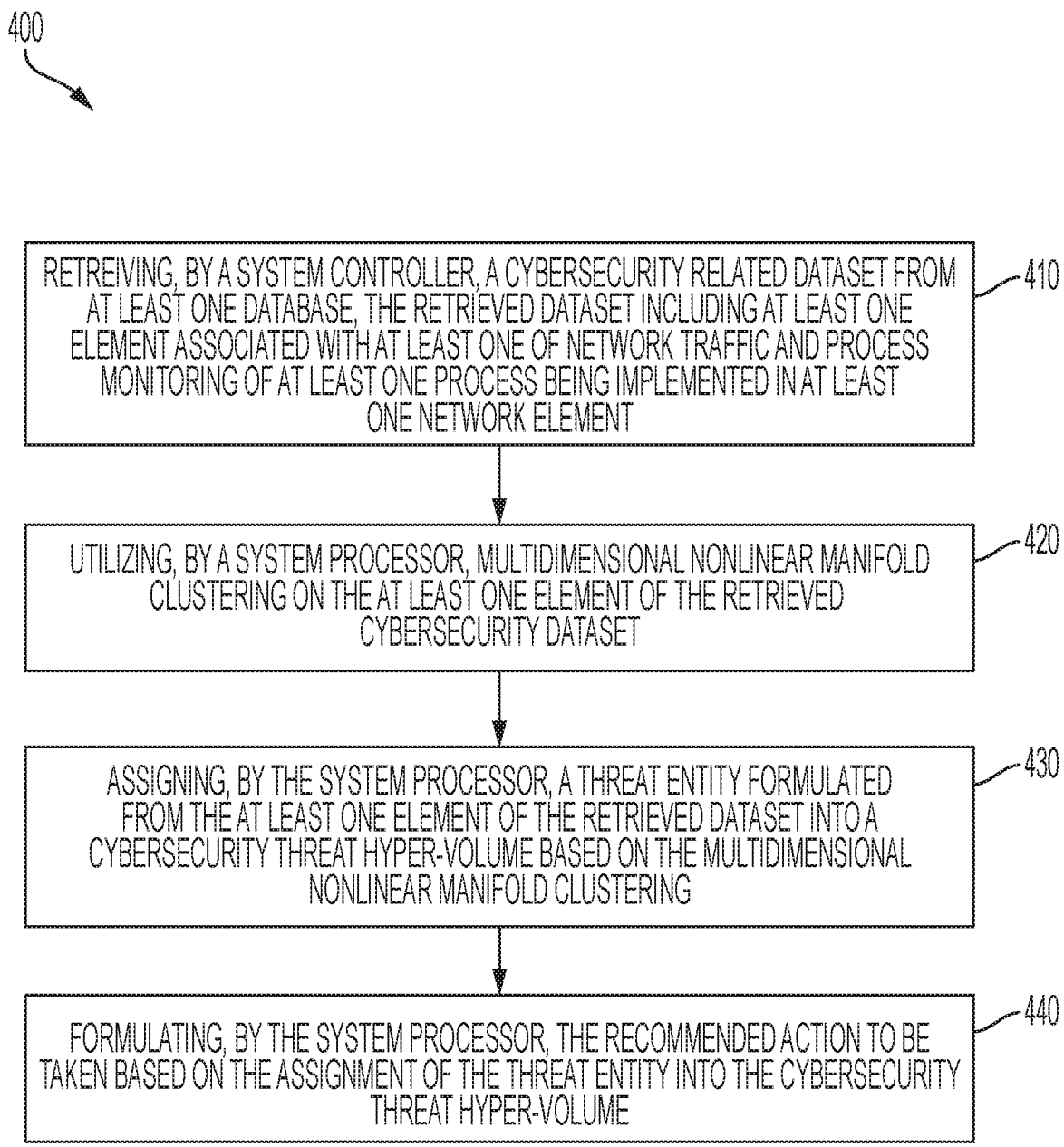
FIG. 4 illustrates an example flowchart for a method of making recommendations for cybersecurity, in accordance with one or more possible embodiments.

FIG. 4 illustrates an example flowchart 400 for making recommendations for cybersecurity, in accordance with one or more possible embodiments. The method 400 can be performed by the CSP 100 and/or performed, either partially or entirely, by any of the other components of the CSP 100, as discussed above. The method 400 is not limited to the example blocks shown and can include any of the processes performed by the CSP 100. The method 400 of determining a recommendation of an action to be taken can begin a block 410. At block 410, a cybersecurity related retrieved dataset can be retrieved, by the system controller 126, from at least one database, the retrieved dataset including at least one element associated with at least one of network traffic and process monitoring of at least one process being implemented in at least one network element. Block 410 proceeds to block 420.

At block 420, multidimensional nonlinear manifold clustering can be utilized, by the system processor 128, on the at least one element from the retrieved dataset. Block 420 proceeds to block 430. At block 430, a threat entity can be assigned, by the system processor 128, into a cybersecurity threat hyper-volume based on the multidimensional nonlinear manifold clustering, the threat entity being formulated from the at least one element of the retrieved dataset. Block 430 proceeds to block 440.

At block 440, a recommended action to be taken can be formulated, by the system processor 128, based on the assignment of the entity into the cybersecurity threat hyper-volume.

While this disclosure has been described with specific embodiments thereof, it is evident that many alternatives, modifications, and variations will be apparent to those skilled in the art. For example, various components of the embodiments may be interchanged, added, or substituted in the other embodiments. Also, all of the processing blocks of each figure may not be necessary for operation of the disclosed embodiments. For example, one of ordinary skill in the art of the disclosed embodiments would be enabled to make and use the teachings of the disclosure by simply employing the elements of the independent claims. Accordingly, embodiments of the disclosure as set forth herein are intended to be illustrative, not limiting. Various changes may be made without departing from the spirit and scope of the disclosure.

In this document, relational terms such as "first," "second," and the like may be used solely to distinguish one entity or action from another entity or action without necessarily requiring or implying any actual such relationship or order between such entities or actions. The phrase "at least one of" followed by a list is defined to mean one, some, or all, but not necessarily all of, the elements in the list. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a," "an," or the like does not, without more constraints, preclude the existence of additional identical elements in the process, method, article, or apparatus that comprises the element. Also, the term "another" is defined as at least a second or more. The terms "including," "having," and the like, as used herein, are defined as "comprising." Furthermore, the background section is written as the inventor's own understanding of the context of some embodiments at the time of filing and includes the inventor's own recognition of any problems with existing technologies and/or problems experienced in the inventor's own work.

The invention claimed is:

1. An apparatus, comprising:
   a system controller to retrieve a cybersecurity dataset from at least one database, the retrieved dataset including at least one element associated with at least one of network traffic and process monitoring of at least one process being implemented in at least one network element; and
   a system processor to utilize multidimensional nonlinear manifold clustering on the at least one element of the retrieved cybersecurity dataset, assign a threat entity formulated from the at least one element of the retrieved dataset into a cybersecurity threat hyper-volume based on the multidimensional nonlinear manifold clustering, and formulate a recommended action to be taken based on the assignment of the threat entity into the cybersecurity threat hyper-volume.

2. The apparatus of claim 1, wherein the network element is at least one of a network firewall, a network switch, a mobile device, a local computer resource, a remote computer resource, a user equipment, and a wireless interface.

3. The apparatus of claim 1, wherein system processor further formulates a recommendation command, in response to formulating the recommended action, that includes at least one of block IP address, block access, block process, block port, isolate, lockout user, slowdown/delay access, slowdown/delay process, alert the network administrator, alert the user, and do not take an action, and the system controller further transmits the recommendation command to at least one of a user equipment, network firewall, network switch, wireless interface, mobile device, local computer resource and remote computer resource.

4. The apparatus of claim 1, wherein the at least one element of the retrieved dataset further includes user background information, network policy, and cybersecurity publications.

5. The apparatus of claim 1, wherein system processor further formulates the threat entity from the at least one element of the retrieved dataset.

6. The apparatus of claim 1, wherein the system processor further performs adjudication to minimize a loss function in order to optimize the assignment of the threat entity by adjusting a decision boundary of the cybersecurity threat hyper-volume.

7. The apparatus of claim 1, wherein the utilization of the multidimensional nonlinear manifold clustering further includes utilizing the multidimensional nonlinear manifold clustering and at least one other type of multidimensional clustering including at least one of linear clustering, linear manifold clustering, and nonlinear clustering.

8. The apparatus of claim 1, wherein the assignment of the threat entity into the cybersecurity threat hyper-volume is further based on at least one other type of multidimensional clustering including at least one of linear clustering, linear manifold clustering, and nonlinear clustering.

9. The apparatus of claim 1, wherein the system processor further performs adjudication to minimize a loss function in order to optimize the assignment of the threat entity by adjusting a decision boundary of the cybersecurity threat hyper-volume for the multidimensional nonlinear manifold clustering and at least one other type of multidimensional clustering including at least one of linear clustering, linear manifold clustering, and nonlinear clustering, and selects at least one of the multidimensional nonlinear manifold clustering and the at least one other type of multidimensional clustering based on a minimum loss function and optimized threat entity assignment.

10. The apparatus of claim 1, wherein the system processor further performs adjudication to control a number of iterations of the selection of the retrieved dataset and compare multiple iterations of the multidimensional nonlinear manifold clustering and at least one other type of multidimensional clustering.

11. The apparatus of claim 1, wherein the system processor further places the threat entity into an entity universe based on direct insertion.

12. The apparatus of claim 1, wherein the system processor further places the threat entity into an entity universe based on Monte Carlo insertion with or without measure of importance.

13. The apparatus of claim 1, wherein the system processor further divides the threat entity into two or more sub-entities.

14. The apparatus of claim 1, wherein the system processor further combines multiple entities into a super-entity.

15. The apparatus of claim 1, wherein the system processor further generates the threat entity using text processing including performing at least one of Information Theoretic, semantic, and syntactic, with the entity generation includes extracting numerically encoded text features from at least one of bulk text, structured text, and unstructured text.

16. The apparatus of claim 1, wherein the threat hyper-volume is a first hyper-volume, the system processor further applies the assignment of the threat entity regionally to a second hyper-volume, the first and second hyper-volumes sharing a decision boundary with each other.

17. The apparatus of claim 1, wherein the system processor further formulates a confidence region to rank an order of a plurality of the recommended action.

18. The apparatus of claim 1, wherein the system processor further ascribes the recommended action to the cybersecurity threat hyper-volume based on at least one of supervised training and unsupervised training.

19. The apparatus of claim 1, wherein the system processor further performs adjudication to formulate at least one of the retrieved dataset and the threat entity, to optimize the recommended action.

20. The apparatus of claim 1, wherein at least one of the system processor and system controller are at least partially implemented in at least one of a local computing, distributed computing, mobile computing, cloud-based computing, Graphics Processing Unit (GPU), array processing, Field Programmable Gate Arrays (FPGA), tensor processing, Application Specific Integrated Circuits (ASIC), quantum computing, and a software program.

21. The apparatus of claim 1, wherein the system controller further transmits to a network equipment the recommended action to be taken in response to a cybersecurity threat.

22. A method, comprising:
retrieving, by a system controller, a cybersecurity dataset from at least one database, the retrieved dataset including at least one element associated with at least one of network traffic and process monitoring of at least one process being implemented in at least one network element;
utilizing, by a system processor, multidimensional nonlinear manifold clustering on the at least one element of the retrieved cybersecurity dataset;
assigning, by the system processor, a threat entity formulated from the at least one element of the retrieved dataset into a cybersecurity threat hyper-volume based on the multidimensional nonlinear manifold clustering; and
formulating, by the system processor, a recommended action to be taken based on the assignment of the threat entity into the cybersecurity threat hyper-volume.

23. The method of claim 22, wherein the network element is at least one of a network firewall, a network switch, a mobile device, a local computer resource, a remote computer resource, a user equipment, and a wireless interface.

24. The method of claim 22, further comprising formulating, by the system processor, a recommendation command, in response to formulating the recommended action, that includes at least one of block IP address, block access, block process, block port, isolate, lockout user, slowdown/delay access, slowdown/delay process, alert the network administrator, alert the user, and do not take an action, and the system controller further transmits the recommendation command to at least one of a user equipment, network firewall, network switch, wireless interface, mobile device, local computer resource and remote computer resource.

25. The method of claim 22, wherein the at least one element of the retrieved dataset further includes user background information, network policy, and cybersecurity publications.

26. The method of claim 22, further comprising formulating, by the system processor, the threat entity from the at least one element of the retrieved dataset.

27. The method of claim 22, further comprising performing adjudication, by the system processor, to minimize a loss function in order to optimize the assignment of the threat entity by adjusting a decision boundary of the cybersecurity threat hyper-volume.

28. The method of claim 22, wherein the utilization of the multidimensional nonlinear manifold clustering further includes utilizing the multidimensional nonlinear manifold clustering and at least one other type of multidimensional clustering including at least one of linear clustering, linear manifold clustering, and nonlinear clustering.

29. The method of claim 22, wherein the assignment of the threat entity into the cybersecurity threat hyper-volume is further based on at least one other type of multidimensional clustering including at least one of linear clustering, linear manifold clustering, and nonlinear clustering.

30. The method of claim 22, further comprising performing adjudication, by the system processor, to minimize a loss function in order to optimize the assignment of the threat entity by adjusting a decision boundary of the cybersecurity threat hyper-volume for the multidimensional nonlinear manifold clustering and at least one other type of multidimensional clustering including at least one of linear clustering, linear manifold clustering, and nonlinear clustering, and selects at least one of the multidimensional nonlinear manifold clustering and the at least one other type of multidimensional clustering based on a minimum loss function and optimized entity assignment.

31. The method of claim 22, further comprising performing adjudication, by the system processor, to control a number of iterations of the selection of the retrieved dataset and compare multiple iterations of the multidimensional nonlinear manifold clustering and at least one other type of multidimensional clustering.

32. The method of claim 22, further comprising placing, by the system processor, the threat entity into an entity universe based on direct insertion.

33. The method of claim 22, further comprising placing, by the system processor, the threat entity into an entity universe based on Monte Carlo insertion with or without measure of importance.

34. The method of claim 22, further comprising dividing, by the system processor, the threat entity into two or more sub-entities.

35. The method of claim 22, further comprising combining, by the system processor, multiple entities into a super-entity.

36. The method of claim 22, further comprising generating, by the system processor, the threat entity using text processing including performing at least one of Information Theoretic, semantic, and syntactic, with the threat entity generation includes extracting numerically encoded text features from at least one of bulk text, structured text, and unstructured text.

37. The method of claim 22, wherein the threat hyper-volume is a first hyper-volume, the method further comprising applying, by system processor, the assignment of the threat entity regionally to a second hyper-volume, the first and second hyper-volumes sharing a decision boundary with each other.

38. The method of claim 22, further comprising formulating, by the system processor, a confidence region to rank an order of a plurality of the recommended action.

39. The method of claim 22, further comprising ascribing, by the system processor, the recommended action to the cybersecurity threat hyper-volume based on at least one of supervised training and unsupervised training.

40. The method of claim 22, further comprising performing adjudication, by the system processor, to formulate at least one of the retrieved dataset and the threat entity, to optimize the recommended action.

41. The method of claim 22, wherein at least one of the system processor and system controller are at least partially implemented in at least one of a local computing, distributed computing, mobile computing, cloud-based computing, Graphics Processing Unit (GPU), array processing, Field Programmable Gate Arrays (FPGA), tensor processing, Application Specific Integrated Circuits (ASIC), quantum computing, and a software program.

42. The method of claim 22, further comprising transmitting, by the system controller, to a network equipment the recommended action to be taken in response to a cybersecurity threat.

* * * * *